(12) United States Patent
Chen et al.

(10) Patent No.: US 10,519,436 B2
(45) Date of Patent: Dec. 31, 2019

(54) METHODS AND COMPOSITIONS FOR GENERATION OF BINDING AGENTS AGAINST CELL SURFACE ANTIGENS

(71) Applicant: X-BODY, INC., Waltham, MA (US)

(72) Inventors: Yan Chen, Lexington, MA (US);
Steven M. Shamah, Waltham, MA (US)

(73) Assignee: X-BODY, INC., Waltham, MA (US)

( * ) Notice: Subject to any disclaimer, the term of this patent is extended or adjusted under 35 U.S.C. 154(b) by 356 days.

(21) Appl. No.: 15/024,002

(22) PCT Filed: Sep. 22, 2014

(86) PCT No.: PCT/US2014/056782
§ 371 (c)(1),
(2) Date: Mar. 22, 2016

(87) PCT Pub. No.: WO2015/042528
PCT Pub. Date: Mar. 26, 2015

(65) Prior Publication Data
US 2016/0244743 A1    Aug. 25, 2016

Related U.S. Application Data

(60) Provisional application No. 61/881,203, filed on Sep. 23, 2013.

(51) Int. Cl.
| | | |
|---|---|---|
| C40B 30/04 | (2006.01) | |
| C12N 15/10 | (2006.01) | |
| C07K 16/28 | (2006.01) | |

(52) U.S. Cl.
CPC ...... *C12N 15/1037* (2013.01); *C07K 16/2869* (2013.01); *C12N 15/1093* (2013.01);
(Continued)

(58) Field of Classification Search
None
See application file for complete search history.

(56) References Cited

U.S. PATENT DOCUMENTS

| | | | |
|---|---|---|---|
| 6,794,128 B2 | 9/2004 | Marks et al. | |
| 2011/0076752 A1* | 3/2011 | Wu | C07K 16/00 435/272 |
| 2014/0113831 A1* | 4/2014 | Chen | G01N 33/6854 506/9 |

FOREIGN PATENT DOCUMENTS

| | | |
|---|---|---|
| CN | 105659090 A | 6/2016 |
| EP | 2 348 052 A2 | 7/2011 |

(Continued)

OTHER PUBLICATIONS

Poul (May 25, 2009) Antibody Phage Display pp. 155 to 163 (hereinafter known as Poul).*

(Continued)

*Primary Examiner* — Christian C Boesen
(74) *Attorney, Agent, or Firm* — Lathrop Gage LLP; James H. Velema, Esq.

(57) ABSTRACT

Provided are methods and compositions for identifying binding polypeptides (e.g., antibodies or antigen binding fragments thereof) that specifically binds to a cell-surface antigen. The methods of the invention generally comprise contacting a variegated nucleic acid-display library of binding polypeptides with a cell-surface antigen displayed on the exterior surface of a cell; and isolating from the library at least one library member that specifically binds to the cell-surface antigen on the exterior surface of the cell. Also provided are novel nucleic acid display libraries (e.g., DNA display libraries) useful in the methods of the invention.

17 Claims, 23 Drawing Sheets

Specification includes a Sequence Listing.

(52) U.S. Cl.
CPC ...... *C07K 2317/21* (2013.01); *C07K 2317/56* (2013.01); *C07K 2317/60* (2013.01); *C07K 2317/77* (2013.01); *C40B 30/04* (2013.01); *G01N 2500/04* (2013.01); *G01N 2500/10* (2013.01)

(56) References Cited

FOREIGN PATENT DOCUMENTS

| JP | 2011-528912 | A  | 12/2011 |
|----|-------------|----|---------|
| WO | 2010/011944 | A2 | 1/2010  |
| WO | 2012/07594  | A1 | 1/2012  |
| WO | 2012/125733 | A2 | 9/2012  |
| WO | 2014/209801 | A1 | 12/2014 |

OTHER PUBLICATIONS

International Search Report with Written Opinion corresponding to International Patent Application No. PCT/US2014/056782, dated Jan. 7, 2015.

Becker et al. (2004) "Ultra-high-throughput screening based on cell-surface display and fluorescence-activated cell sorting for the identification of novel biocatalysts," Current Opinion in Biotechnology. 15(4):323-329.

Bowers et al. (2011) "Coupling mammalian cell surface display with somatic hypermutation for the discovery and maturation of human antibodies," Proc. Natl. Acad. Sci. USA. 108(51):20455-20460.

Wittrup (2001) "Protein engineering by cell-surface display," Current Opinion in Biotechnology. 12:395-399.

* cited by examiner

FIG. 11    Lead criteria built into the selection process.

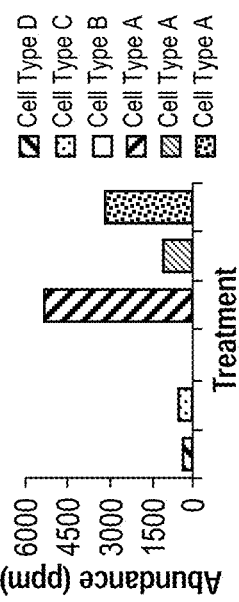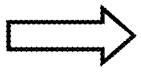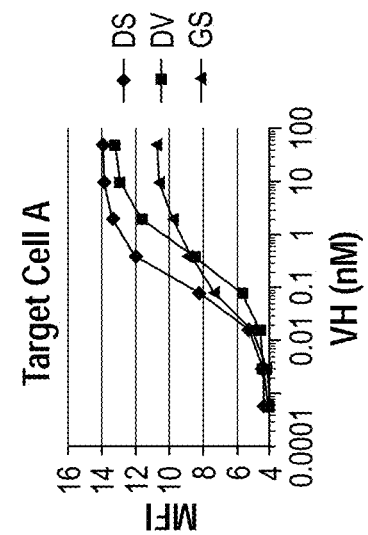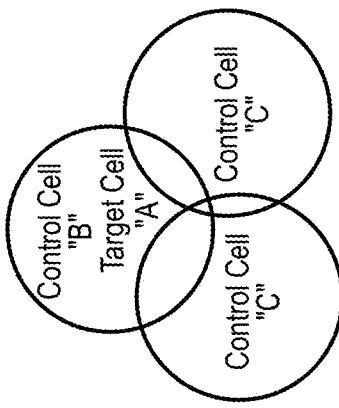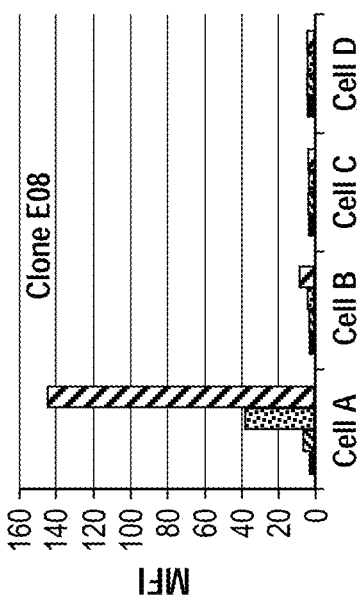
Fig. 18

METHODS AND COMPOSITIONS FOR GENERATION OF BINDING AGENTS AGAINST CELL SURFACE ANTIGENS

RELATED APPLICATIONS

This application is a 35 U.S.C. § 371 filing of International Application No. PCT/US2014/056782, filed Sept. 22, 2014, which claim priority to U.S. Provisional Application No. 61/881,203, filed Sep. 23, 2013, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 21, 2016, is named 579587_XBI-009US_SL.txt and is 6,990 bytes size.

BACKGROUND

Binding polypeptides, such as antibodies and fragments thereof, are commercially important as therapeutic and diagnostic agents. Traditional methods of screening for binding polypeptide generally employ soluble antigens. However, for certain cell-surface antigens, conformational epitopes on these antigens are altered when the antigens are solubilized from the plasma membrane, resulting in a failure to generate binding polypeptides that can recognize the native antigen. Accordingly, there is a need in the art for novel methods of screening for binding polypeptides that can specifically bind to cell-surface antigens in their native conformation.

SUMMARY

The invention provides methods and compositions for identifying binding polypeptides (e.g., antibodies or antigen binding fragments thereof) that specifically binds to a cell-surface antigen. The methods of the invention generally comprise contacting a variegated nucleic acid-display library of binding polypeptides with a cell-surface antigen displayed on the exterior surface of a cell; and isolating from the library at least one library member that specifically binds to the cell-surface antigen on the exterior surface of the cell. The methods and compositions of the invention are particularly advantageous in that they allow for the rapid identification of binding polypeptides that bind to native forms of the target cell surface antigen, and binding polypeptides that possess novel epitope specificity and functional properties (e.g. internalization, agonism, antagonism, or allosteric modulatory properties). These methods and compositions also allow for identification of novel, therapeutically useful cell-type specific antigens or epitopes. Also provided are novel V-domain (e.g., VH and/or VL domain) nucleic acid display libraries (e.g., DNA display libraries) that can be used to screen for novel binding polypeptides.

BRIEF DESCRIPTION OF THE DRAWINGS

FIG. 4 discloses SEQ ID NOS 19, 20, 20-24, 19, 21, 25, 22, 22, 25, 26, 24, 20, 19, 20, 20, 27, 27, 23, 24, 28, 21, 25, 27, 28, 25, 26, 24,and 20, respectively, in order of appearance.

FIG. 18 is a schematic of an exemplary parallel screen identifying VH domains that bind specifically to human disease cells. Live cell selection was used to identify targets or epitopes that are specifically expressed on distinct cellular populations, including disease patient vs normal human cells. Cell type-specific selection strategies were applied and deep sequencing used to identify VH domains enriched with predicted binding specificity profiles. High affinity (pM) binders were isolated that demonstrate disease cell-specific binding profiles as measured by FACS.

DETAILED DESCRIPTION

Figure 1:
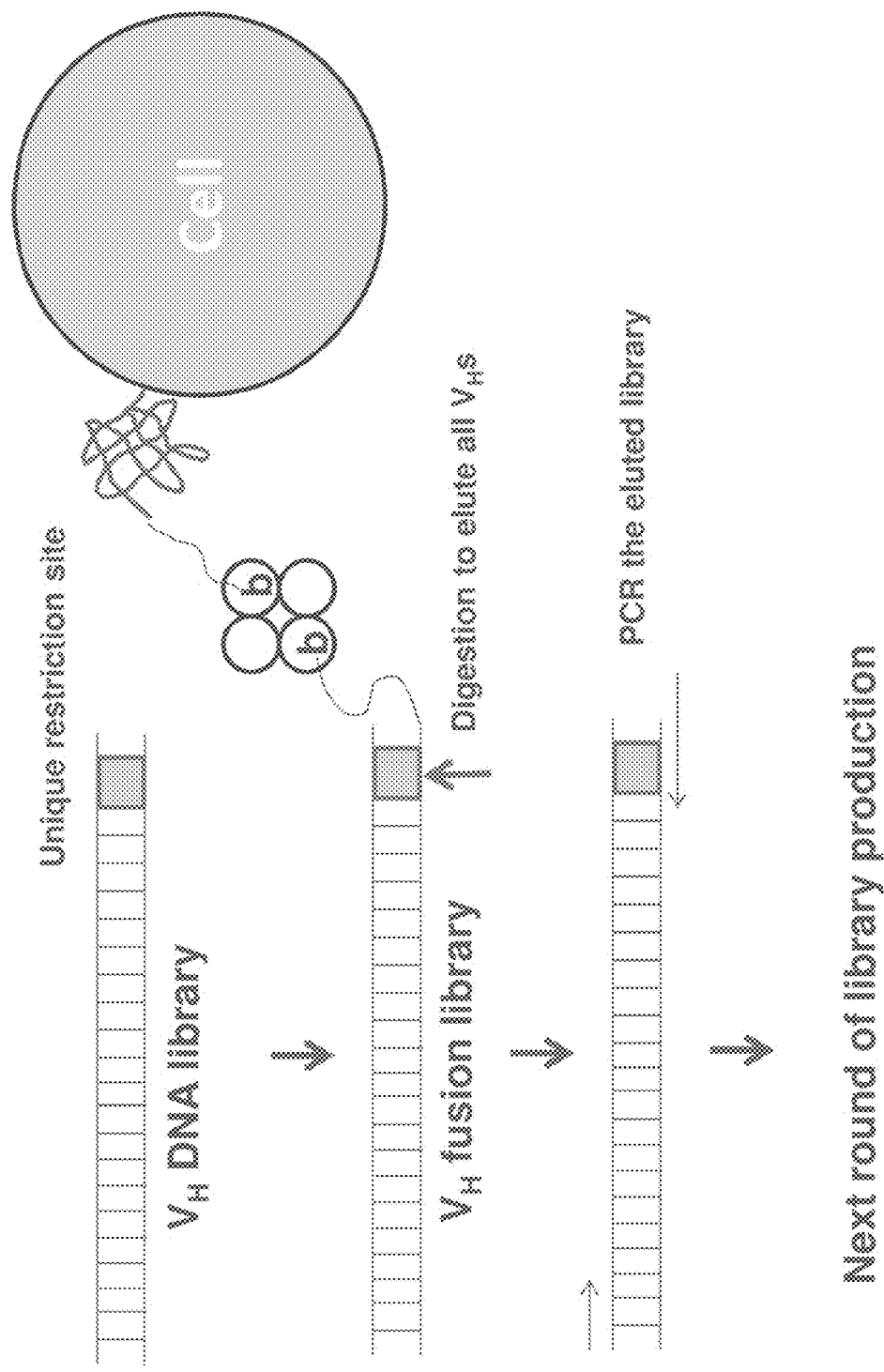
FIG. 1 is a schematic of exemplary DNA display compositions and screening methods of the invention.

The invention provides methods and compositions for identifying binding polypeptides (e.g., antibodies or antigen binding fragments thereof) that specifically binds to a cell-surface antigen. The methods of the invention generally comprise contacting a variegated nucleic acid-display library of binding polypeptides with a cell-surface antigen displayed on the exterior surface of a cell; and isolating from the library at least one library member that specifically binds to the cell-surface antigen on the exterior surface of the cell. The methods and compositions of the invention are particularly advantageous in that they allow for the rapid identification of binding polypeptides that bind to native forms of the target cell surface antigen, and binding polypeptides that possess novel epitope specificity and functional properties (e.g. internalization, agonism, antagonism, or allosteric modulatory properties). These methods and compositions also allow for identification of novel, therapeutically useful cell-type specific antigens or epitopes. Also provided are novel V-domain (e.g., VH and/or VL domain) nucleic acid display libraries (e.g., DNA display libraries) that can be used to screen for novel binding polypeptides.

I. DEFINITIONS

As used herein, the term "nucleic acid display library" refers to any art recognized in vitro cell-free phenotype-genotype linked display, including, without limitation those set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; 6,348,315, WO2012125733 and WO2010/011944, which are all hereby incorporated by reference in their entirety.

As used herein, the term "antigen" refers to the molecule recognized by a binding polypeptide.

As used herein, the term "specifically binds to" refers to the ability of a binding molecule (e.g., a VH or VL domain) to bind to an antigen with an affinity of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or bind to a target with an affinity that is at least two-fold greater than its affinity for a nonspecific antigen.

As used herein, the term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated VH) and a heavy chain constant region. The heavy chain constant region comprises three domains, CH1, CH2 and CH3. Each light chain comprises a light chain variable region (abbreviated VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR).

As used herein, the term "antigen-binding portion" of an antibody includes any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding portion."

As used herein, the term "V domain" refers to a single polypeptide comprising a VH domain or VL domain that is devoid of constant region sequences that facilitate the covalent pairing of said VH domain or VL domain with a complementary VL domain or VH domain, respectively.

As used herein, the terms "VH domain" and "VL domain" refer to single antibody variable heavy and light domains, respectively, comprising FR (Framework Regions) 1, 2, 3 and 4 and CDR (Complementary Determinant Regions) 1, 2 and 3 (see Kabat et al. (1991) Sequences of Proteins of Immunological Interest. (NIH Publication No. 91-3242, Bethesda).

As used herein, the term "FR1-FR3" refers to the region of a VH encompassing FR1, CDR1, FR2, CDR2 and FR3, but excluding the CDR3 and FR4 regions.

As used herein, the term "CDR3-FR4" refers to the region of a VH encompassing CDR3 and FR4, but excluding the FR1, CDR1, FR2, CDR2 and FR3 regions.

As used herein with respect to antibody variable domains, the term "chimeric" refers to an antibody variable domain comprising amino acid sequences from two or more different antibody variable domain, e.g., a variable domain with CDR3 sequences from a reference antibody and FR1-FR3 sequences from one or more different antibodies.

II. CELL SURFACE ANTIGENS

In certain aspects, the invention provides methods of identifying a binding polypeptide that specifically binds to a cell-surface antigen.

Any antigen that is capable of being displayed on the surface of a cell can be employed in the methods of the invention, including without limitation, protein, glycan, and/or lipid antigens. In certain embodiments, the antigen is a naturally occurring molecule. Suitable, non-limiting examples of naturally occurring antigens include transmembrane proteins (e.g., G-protein coupled receptors) and GPI-anchored proteins. In certain embodiments, the antigen is a non-naturally occurring recombinant or synthetic antigen. Suitable, non-limiting examples of naturally occurring antigens include, without limitation, chimeric antigens comprising portions from different antigen molecules. In certain embodiments, the identity of the antigen is known prior to preforming the methods of the invention. In certain embodiments, the identity of the antigen is unknown prior to preforming the methods of the invention.

In certain embodiments, the antigen is a transmembrane protein. In certain embodiments, the antigen is a multispan transmembrane protein (e.g., G protein coupled receptors (GPCRs) and ion channels). Non-limiting examples of target antigens include, without limitation, glucagon receptor (GCGR), CXCR1, CXCR2, CXCR3, CXCR4, CXCR6, CCR1, CCR2, CCR3, CCR4, CCR5, CCR6, CCR8, CFTR, CIC-1, CIC-2, CIC-4, CIC-5, CIC-7, CIC-Ka, CIC-Kb, Bestrophins, TMEM16A, GABA receptor, glycin receptor, ABC transporters, NAV1.1, NAV1.2, NAV1.3, NAV1.4, NAV1.5, NAV1.6, NAV1.7, NAV1.8, NAV1.9, sphingosin-1-phosphate receptor (S1P1R), and NMDA channels. In certain embodiments, the antigen is a human antigen. In certain embodiments, the antigen is GCGR, CXCR4, or NAV1.7 (e.g., human GCGR, CXCR4, or NAV1.7).

The cell surface antigens employed in the methods of the invention can be displayed on any cell or cell-like particle (e.g., lipid vesicle). In certain embodiments, the cell is a cell type that naturally expresses the cell-surface antigen. In certain embodiments, the cell is a recombinant cell that is engineered to heterologously express the cell-surface antigen. In certain embodiments, the cell is a disease-associated variant of a normal cell (e,g, a tumor cell).

III. BINDING POLYPEPTIDES

In certain aspects, the invention provides methods of identifying a binding polypeptide that specifically binds to a cell-surface antigen.

Any type of binding polypeptide can be employed in the methods of the invention including, without limitation, antibodies, or fragments thereof, and immunoglobulin-like domains. Suitable immunoglobulin-like domains include, without limitation, fibronectin domains (see, for example, Koide et al. (2007), *Methods Mol. Biol.* 352: 95-109, which is incorporated by reference herein in its entirety), DARPin (see, for example, Stumpp et al. (2008) *Drug Discov. Today* 13 (15-16): 695-701, which is incorporated by reference herein in its entirety), Z domains of protein A (see, Nygren et al. (2008) *FEBS J.* 275 (11): 2668-76, which is incorporated by reference herein in its entirety), Lipocalins (see, for example, Skerra et al. (2008) *FEBS J.* 275 (11): 2677-83, which is incorporated by reference herein in its entirety), Affilins (see, for example, Ebersbach et al. (2007) *J. Mol. Biol.* 372 (1): 172-85, which is incorporated by reference herein in its entirety), Affitins (see, for example, Krehenbrink et al. (2008). *J. Mol. Biol.* 383 (5): 1058-68, which is incorporated by reference herein in its entirety), Avimers (see, for example, Silverman et al. (2005) *Nat. Biotechnol.* 23 (12): 1556-61, which is incorporated by reference herein in its entirety), Fynomers, (see, for example, Grabulovski et al. (2007) *J Biol Chem* 282 (5): 3196-3204, which is incorporated by reference herein in its entirety), and Kunitz domain peptides (see, for example, Nixon et al. (2006) *Curr Opin Drug Discov Devel* 9 (2): 261-8, which is incorporated by reference herein in its entirety).

In certain embodiments, the binding polypeptide is an antibody VH or VL domain.

IV. NUCLEIC ACID DISPLAY LIBRARIES

In certain aspects, the methods of the invention employ nucleic acid-display libraries. In one aspect, the invention provides a variegated nucleic acid-display library of chimeric V domains (e.g., VH or VL domains), each member of the library comprising FR1-FR3 region sequences from a first antibody and CDR3-FR4 region sequences from a second antibody. Exemplary libraries are disclosed herein, for example, in Example 2. The libraries disclosed herein are suitable for use in any of the methods disclosed herein.

The libraries of the invention can comprise VH or VL domain sequences from any source or species. In certain embodiments, the FR1-FR3 region sequences are from the immunological repertoire of a naïve human. In certain embodiments, the CDR3-FR4 region sequences are from the immunological repertoire of a naïve human. In certain embodiments, the V domains are VH domains (e.g., human VH domains).

In certain embodiments, the library is preselected for binding to an antigen, such that each member of the library binds to the same antigen. In certain embodiments, each member of the library binds to GCGR, CXCR4, or NAV1.7 (e.g., human GCGR, CXCR4, or NAV1.7).

In certain embodiments, the library comprises at least $10^2$ (e.g., at least $10^2$, $10^3$, $10^4$, $10^5$, $10^6$, $10^7$, $10^8$, $10^9$, $10^{10}$, $10^{11}$, $10^{12}$, $10^{13}$, $10^{14}$, or $10^{15}$) unique V domains (e.g., VH domains).

The libraries of the invention can be made using any art recognized methods. In certain embodiments, the library is generated (e.g., by PCR) using at least one oligonucleotide having a sequence selected from the group consisting of SEQ ID No: 1, 2, 3, 4, 5, 6, 7, 8, 9, 10, 11, 12, 13, 14, 15, 16, 17, and 18.

In one aspect, the invention provides one or more oligonucleotide (e.g., a DNA oligonucleotide) having a sequence selected from the group consisting of SEQ ID No: 1, 2, 3, 4, 5, 6, 7, 8, 9, 10, 11, 12, 13, 14, 15, 16, 17, and 18.

V. CELL SURFACE DISPLAY METHODS

In certain aspects, the invention provides a method of identifying a binding polypeptide that specifically binds to a cell-surface antigen. The method generally comprises: (a) contacting a variegated nucleic acid-display library of binding polypeptides with a cell-surface antigen displayed on the exterior surface of a first cell type; and (b) isolating from the library at least one library member that specifically binds to the cell-surface antigen on the exterior surface of the first cell type. In certain embodiments, prior to step (a), the variegated nucleic acid-display library of binding polypeptides is contacted with a second cell type that does not display the antigen displayed on the exterior surface, in order to pre-clear the library of binding polypeptides that do not specifically bind to the antigen.

In certain aspects, the invention provides a method of identifying a binding polypeptide that specifically binds to a cell-surface antigen. The method generally comprises: (a) contacting a variegated nucleic acid-display library of binding polypeptides with a first cell type expressing a cell-surface antigen, and isolating from the library at least one library member that specifically binds to the first cell type; (b) contacting the variegated nucleic acid-display library of binding polypeptides with a second cell type that does not express the cell surface antigen, and isolating from the library at least one library member that specifically binds to the second cell type; and (c) selecting library members that specifically bind to the first cell type but not to the second cell type. In certain embodiments, step (a) and (b) are performed in parallel using separate aliquots of the library to identify binders selective for the first or second cell type, as predicted by deep sequencing analysis of the frequency of a VH sequence binding to both cell types.

The first and second cell types can be closely or distantly related cell types of the same or a different species. In certain embodiments, the second cell type is closely related to the first cell type. For example, the second cell type can be a cell type from the same species and lineage but from a different stage of maturation from the first cell type. Alternatively, the second cell type can be isogenic with the first cell type, differing only in the expression of the target antigen. In certain embodiments, the second cell type is isogenic to the first cell type but expresses an orthologue of the target antigen expressed in the first cell type (e.g., an equivalent antigen from a different species). The use of such closely related cell types as counter-selections allows for the selection of binding polypeptides (e.g., V domains) that bind to the desired target without any cross reactivity to related antigen orthologues. Alternatively, the use of closely related cell types in co-selection assays allows for the selection of binding polypeptides (e.g., V domains) that bind to the desired target and also cross react with related antigen orthologues. This co-selection approach is useful for generating binding polypeptides (e.g., V domains) that bind to both human target antigens and the mouse or simian orthologues, avoiding the need to produce surrogate binding polypeptides (e.g., V domains) for animal studies.

Suitable nucleic acid-display libraries for use in the methods of the invention are set forth in, for example, U.S. Pat. Nos. 7,195,880; 6,951,725; 7,078,197; 7,022,479; 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; 6,348,315; WO2012125733 and WO2010/0119, which are all hereby incorporated by reference in their entirety. In certain embodiments, the variegated nucleic acid-display library is a DNA display library. In certain embodiments, the nucleic acid-display library is a DNA display library described herein or in WO2012125733 and/or WO2010/011944, which are both hereby incorporated by reference in their entirety.

In certain embodiments, each member of the DNA-display library comprises a binding polypeptide linked through an intervening DNA linker to a DNA coding sequence encoding the binding polypeptide, wherein the DNA linker comprises a restriction endonuclease site (see e.g., FIG. 1). Any restriction endonuclease site can be employed. In one particular embodiment, the restriction endonuclease site is not present in the DNA coding sequence of members of the DNA-display library, thus avoiding cleavage of the DNA coding sequence upon restriction endonuclease digestion of the library members. In one particular embodiment, the restriction endonuclease site is a Not1 site.

In certain embodiments, it is desirable to physically separate the DNA coding sequence of the isolated library members from the linked binding polypeptide. Any methods of physical separation can be employed. Where the isolated library members comprise a DNA linker comprising a restriction endonuclease site (see e.g., FIG. 1), the physical separation can be achieved by restriction endonuclease digestion of the isolated library members. The resultant liberated DNA coding sequences can be further separated from the cell/binding polypeptide complexes by any art recognized method, e.g., centrifugation.

In certain embodiments, it is desirable to physically separate the intact isolated library members from the from the first and/or second cell type. Any methods of physical separation can be employed. In certain embodiments, the isolated library members are separated from the first or second cell type by elution with a ligand (e.g., a natural ligand) of the target antigen. In certain embodiments, the isolated library members are separated from the first or second cell type by enzymatic cleavage of the cell-surface antigen. Any methods of enzymatic cleavage of the antigen can be employed, e.g., protease, lipase, and/or glycosidase enzymatic cleavage. In certain embodiments, where the cell-surface antigen is attached to the cell surface by a glycolipid anchor, the isolated library members are separated from the first or second cell type by phospholipase cleavage of the glycolipid anchor. The resultant, liberated library members can be further separated from the first or second cell type by any art recognized method, e.g., centrifugation.

Once the library members that specifically bind to the first and/or second cell type have been isolated, the DNA coding sequence of these molecules can be determined. Accordingly, in certain embodiments, the methods of the invention further comprise the step of determining the DNA coding sequence of at least a portion of the isolated library members. Any art recognized means for DNA sequence determination can be employed. In one particular embodiment, the DNA coding sequence is determined by single molecule, deep sequencing techniques (e.g., pyrosequencing). Single molecule, deep sequencing techniques are well known in the art (see e.g., those described in U.S. Pat. No. 6,210,891, which is hereby incorporated by reference in its entirety). In certain embodiments, where the binding polypeptides are antibodies, or antigen binding fragments thereof, the DNA coding sequence of the CDR3 region is determined. In certain embodiments, the DNA coding sequences of the library member that bind to the first and second cell types are determined. Library members that specifically bind to the first cell type but not to the second cell type are considered to comprise binding polypeptides that specifically bind to an antigen specific for the first cell type.

Once a binding polypeptide that specifically binds to the cell-surface antigen has been identified, it can be heterologously expressed in vitro (e.g., in cells or in a cell-free expression system) or in vivo (e.g., in a transgenic animal). Accordingly, in certain embodiments, the methods of the invention further comprise the step of heterologously expressing in vitro (e.g., in cells or in a cell-free expression system) or in vivo (e.g., in a transgenic animal), the identified binding polypeptide.

In certain embodiments, the identity of the antigen is known prior to preforming the methods of the invention. However, it is not necessary to know the identity of the antigen. Indeed, in certain embodiments, the identity of the antigen is unknown prior to preforming the methods of the invention. Thus, in this latter case, the methods of the invention allow for the identification of novel antigens and epitopes present on the surface of a cell type of interest (e.g., a tumor cell).

In certain embodiments, the methods disclosed herein comprise the selection of binding polypeptides that are capable of functional internalization upon binding to the cell surface antigen. Such binding polypeptides are particularly useful in the production of drug conjugates because they allow for the delivery of a cytotoxic drug to the interior of a target cell. Any methodology for screening for functional internalization can be employed. For example, the variegated nucleic acid-display library of binding polypeptides can be contacted with target cells under conditions that to allow for binding polypeptide internalization (e.g., for about for 1-2 hours at 37° C.). The cells can then washed and lysed with cell lysis buffer in the presence of protease inhibitors. The internalized library members can then be ethanol precipitated and the DNA coding sequences enriched by PCR amplification.

The methods disclosed herein can be applied to any target epitope discovery process. For example, target epitopes can include: homing domains for inflammation; tumor specific target epitopes from primary tumors with or without resistance to treatment, tumor cell lines, and tumors that harbor any mutations that may result in neoepitopes; and other disease specific epitopes that mediate disease specific malfunction and be targeted for biologic therapy.

VI. ANTIGEN SOLUBILIZATION

In certain aspects, the methods of the invention involve solubilization of antigens (e.g., cell surface antigens, e.g., a GPCR) from cells using surfactants that can maintain the native conformation of the antigen and allow for recovery of complexes of binding polypeptides (e.g., VH or VL domains) and antigen. These methods are particular useful for selecting binding polypeptides (e.g., VH domains) that bind to the native conformation of cell surface antigens, (e.g., GPCR).

In one aspect, the invention provides a method of identifying a binding polypeptide (e.g., VH or VL domain) that specifically binds to a cell-surface antigen. The method generally comprises: contacting a first cell type, that displays the cell-surface antigen on the exterior surface, with a variegated nucleic acid-display library of binding polypeptides, such that a population of binding polypeptides/antigen complexes is formed; contacting the first cell type with a surfactant, such that the population of binding polypeptides/antigen complexes is solubilized; and isolating the solubilized population of binding polypeptides/antigen complexes.

In certain embodiments, the solubilized population of binding polypeptides/antigen complexes are isolated using a binding agent specific for a portion of the binding polypeptide. Any binding agent that binds to the native polypeptide can be used in this method. Suitable binding agents include, without limitation, antibodies specific for the polypeptide (or an epitope tag genetically fused to the polypeptide).

In certain embodiments, binding agents specific for a specific activation state can be used to isolate the population of binding polypeptides/antigen complexes. Suitable binding agents include, without limitation, antibodies specific for a chemically modified (e.g., a phosphorylated) variant of the antigen (e.g., phosphor-specific antibodies).

In certain embodiments, binding agents specific for accessory molecules that associate with the antigen during a specific activation state (e.g., cytosolic signaling molecules or co-receptors) can be used to isolate the population of binding polypeptides/antigen complexes.

Any surfactant that can extract the antigen from the cell membrane and maintain the native conformation of the antigen can be employed in the methods of the invention. Suitable surfactants include, without limitation, n-dodecyl-β-d-maltoside (DDM) and 3-[(3-cholamidopropyl)dimethylammonio]-1-propanesulfonate (CHAPS). In certain embodiments, the antigen or the population of binding polypeptides/antigen complexes is solubilized using a mixture of DDM and CHAPS.

Any cell surface antigen known in the art (including those disclosed herein) can be isolated using this method. Any cell type known in the art (including those disclosed herein) can be employed in this method. Any nucleic acid display library known in the art (including those disclosed herein) can be employed in this method. Any binding polypeptide or small molecule known in the art (including those disclosed herein) can be screened for binding to a cell-surface antigen this method.

VII. INTERNALIZATION

In certain aspects, the methods of the invention involve selection of binding polypeptides that specifically bind to a desired cell-surface antigen and are internalized along with the antigen. Such methods are particular useful for producing binding polypeptides that can deliver payloads (e.g., chemotoxins) into a cell.

In one aspect, the invention provides a method of identifying an internalizing binding polypeptide (e.g., VH or VL domain) that specifically binds to a cell-surface antigen. The method generally comprises: contacting, a first cell type that displays the cell-surface antigen on the exterior surface, with a variegated nucleic acid-display library of binding polypeptides, under conditions that allow for internalization of the cell-surface antigen, and such that a population of internalized binding polypeptides/antigen complexes is formed; washing the first cell type to remove library members bound to the exterior surface; and isolating the internalized binding polypeptides/antigen complexes.

In certain embodiments, the internalized binding polypeptides/antigen complexes are isolated by surfactant extraction. Any surfactant that can extract the antigen from the cell membrane and maintain the native conformation of the antigen can be employed in the methods of the invention. Suitable surfactants include, without limitation, n-dodecyl-β-d-maltoside (DDM) and 3-[(3-cholamidopropyl)dimethylammonio]-1-propanesulfonate (CHAPS). In certain embodiments, the antigen or the population of binding polypeptides/antigen complexes is solubilized using a mixture of DDM and CHAPS.

In certain embodiments, the internalized binding polypeptides/antigen complexes are further isolated using a binding agent specific for a portion of the binding polypeptide. Suitable binding agents include, without limitation, antibodies specific for a chemically modified (e.g., a phosphorylated) variant of the antigen (e.g., phosphor-specific antibodies). In certain embodiments, binding agents specific for accessory molecules that associate with the antigen during a specific activation state (e.g., cytosolic signaling molecules or co-receptors) can be used to isolate the population of binding polypeptides/antigen complexes.

In certain embodiments, the internalized binding polypeptides are further isolated by precipitation of the nucleic acid encoding the binding polypeptides (e.g., by ethanol precipitation).

The library members bound to the exterior surface of the first cell type can be removed using any suitable wash buffer. In certain embodiments, library members bound to the exterior surface of the first cell type are removed by washing with a low pH solution (e.g., a solution with a pH less than about 5, e.g., less than about pH 4, less than about pH 3, or less than about pH 2). Suitable low pH solutions include HCl or glycine at less than pH 3. In certain embodiments, the low pH solution is 0.1 M HCl at about pH 2.7.

In certain embodiments, where multiple rounds of screening are employed, the internalized binding polypeptides are isolated by precipitation of the nucleic acid encoding the binding polypeptides (e.g., by ethanol precipitation) in the initial rounds of screening, and isolated using a binding agent specific for a portion of the binding polypeptide in one or more (more stringent) later round of screening.

Any cell surface antigen known in the art (including those disclosed herein) can be isolated using this method. Any cell type known in the art (including those disclosed herein) can be employed in this method. Any nucleic acid display library known in the art (including those disclosed herein) can be employed in this method. Any binding polypeptide or small molecule known in the art (including those disclosed herein) can be screened for binding to a native cell-surface antigen this method.

VIII. ANTIGEN STEERING

In certain aspects, the methods of the invention involve selection of binding polypeptides that specifically bind to an antigen at a different epitope to that recognized by a reference binding agent (e.g., antibody). Such methods are particular useful for producing binding polypeptides with novel functional properties.

In one aspect, the invention provides a method of method of identifying a binding polypeptide (e.g., VH or VL domain) that specifically binds to an antigen at a different epitope to that recognized by a reference binding agent (e.g., antibody). The method generally comprises: contacting the antigen with a reference binding agent under condition such that a complex of the antigen and reference binding agent (e.g., antibody) is formed; contacting the complex of the antigen and reference antibody with a variegated nucleic acid-display library of binding polypeptides, such that at least one binding polypeptide/antigen complex is formed; and isolating from the library at least one library member that specifically binds to the antigen.

Any cell surface antigen known in the art (including those disclosed herein) can be isolated using this method. Any cell type known in the art (including those disclosed herein) can be employed in this method. Any nucleic acid display library known in the art (including those disclosed herein) can be employed in this method. Any binding polypeptide or small molecule known in the art (including those disclosed herein) can be screened for binding to a native cell-surface antigen this method.

In certain embodiments, the antigen is a cell-surface antigen displayed on the exterior surface of a cell (e.g., a cell surface receptor, such as a GPCR). In certain embodiments, the antigen is GCGR, CXCR4, or NAV1.7 (e.g., human GCGR, CXCR4, or NAV1.7).

IX. BIASING FOR ANTIGEN ACTIVATION STATE

In certain aspects, the methods of the invention involve selection of a binding polypeptide that specifically binds to a desired activation state of an antigen (e.g., a cell-surface antigen). Such methods are particular useful for producing binding polypeptides that allosterically modulate (e.g., inhibit) the target antigen.

In one aspect, the invention provides a method of identifying an internalizing binding polypeptide (e.g., VH or VL domain) that specifically binds to a desired activation state of a cell-surface antigen. The method generally comprises: contacting a first cell type, that displays the cell-surface antigen on the exterior surface, with i) a binding agent that specifically binds to, and modulates the activation state of the cell-surface antigen; and ii) a variegated nucleic acid-display library of binding polypeptides; and isolating from the library at least one library member that specifically binds to the cell-surface antigen on the exterior surface of the first cell type.

Any modulator of the antigen can be employed in the methods of the invention, including agonists, antagonists, partial agonists and the like. In certain embodiments, the modulator is a natural ligand of the antigen. In certain embodiments, the modulator locks the antigen into an inactive conformation.

Any cell surface antigen known in the art (including those disclosed herein) can be isolated using this method. Any cell type known in the art (including those disclosed herein) can be employed in this method. Any nucleic acid display library known in the art (including those disclosed herein) can be employed in this method. Any binding polypeptide or small molecule known in the art (including those disclosed herein) can be screened for binding to a native cell-surface antigen this method.

X. ANTIBODY FORMATS

The VH and/or VL domains employed in the methods of the invention can be used in isolation or fused to additional amino acids (e.g., epitope tags) and/or domains. In certain embodiments, at least one VH domain in a library is fused to at least one CH1 domain, CH2 domain, CH3 domain or a combination thereof. In a particular embodiment, at least one VH domain in a library is fused to at least one heavy chain constant region comprising at least one CH1 domain, CH2 domain and CH3 domain. In certain embodiments, at least one VL domain in a library is fused to at least one light chain constant region.

VH or VL domains identified using the methods disclosed herein can also be subject to further screening methods to select for complimentary VH/VL pairs using, for example, the methods described in WO2012125733 (which is hereby incorporated by reference in its entirety).

VH or VL domains, and/or VH/VL pairs selected using the methods of the invention can be incorporated into another antibody format including, without limitation, scFv, Fab, and/or complete tetrameric antibody.

XI. EXEMPLIFICATION

EXAMPLE 1

Figure 4:
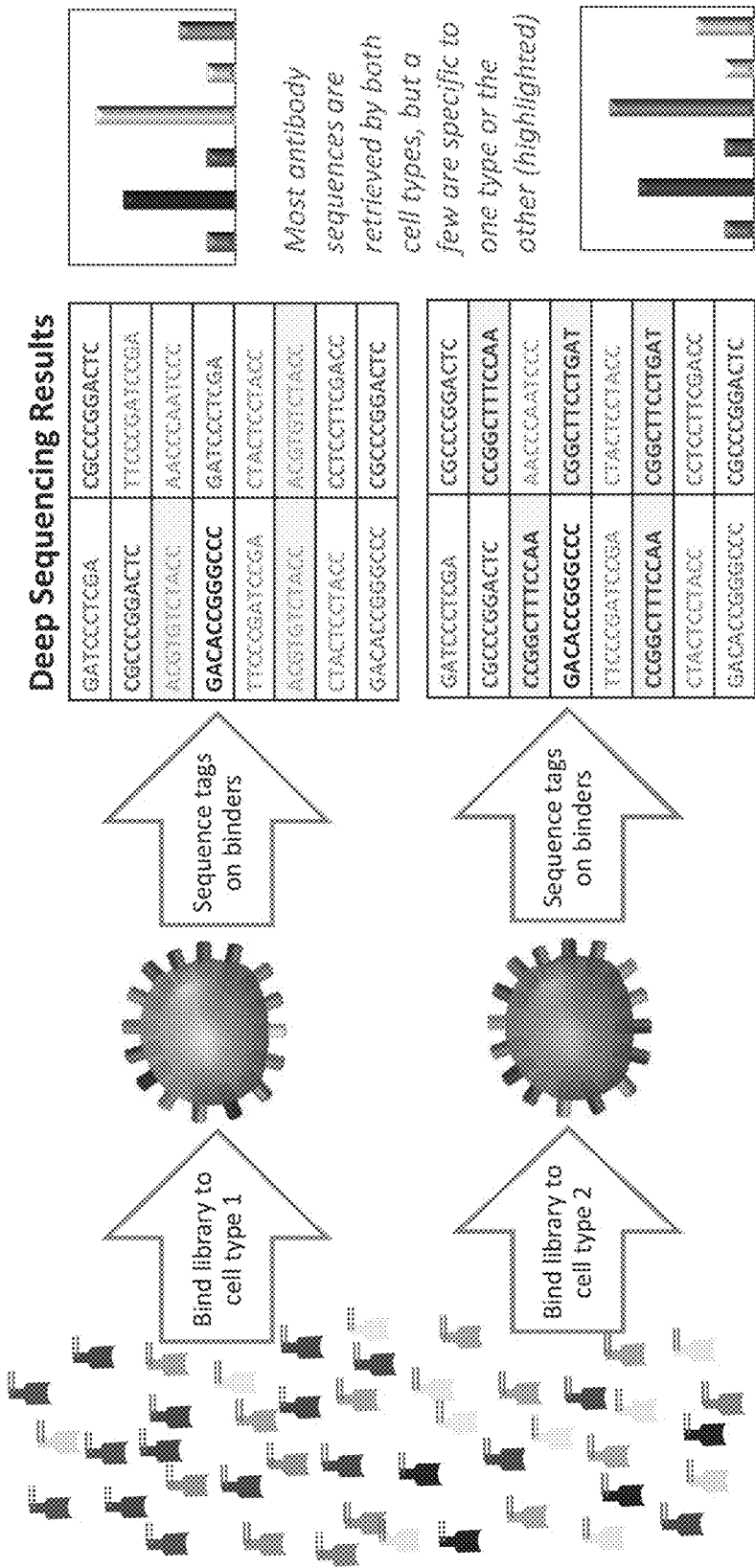
FIG. 4 is a schematic of exemplary parallel selection and deep sequencing strategies employed in the methods of the invention.
Figure 5:
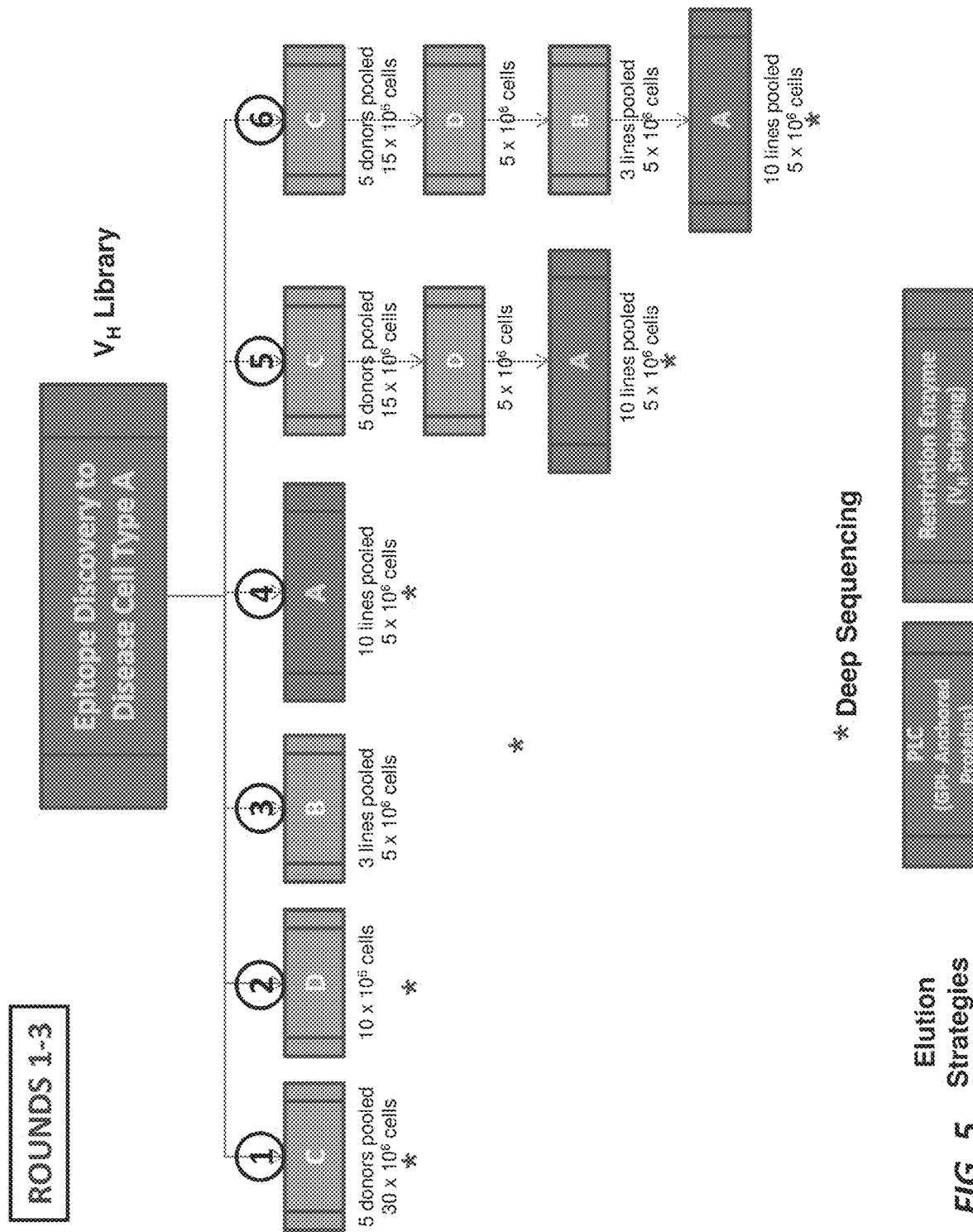
FIG. 5 is a schematic of exemplary parallel selection and deep sequencing strategies employed in the methods of the invention.
Figure 6:
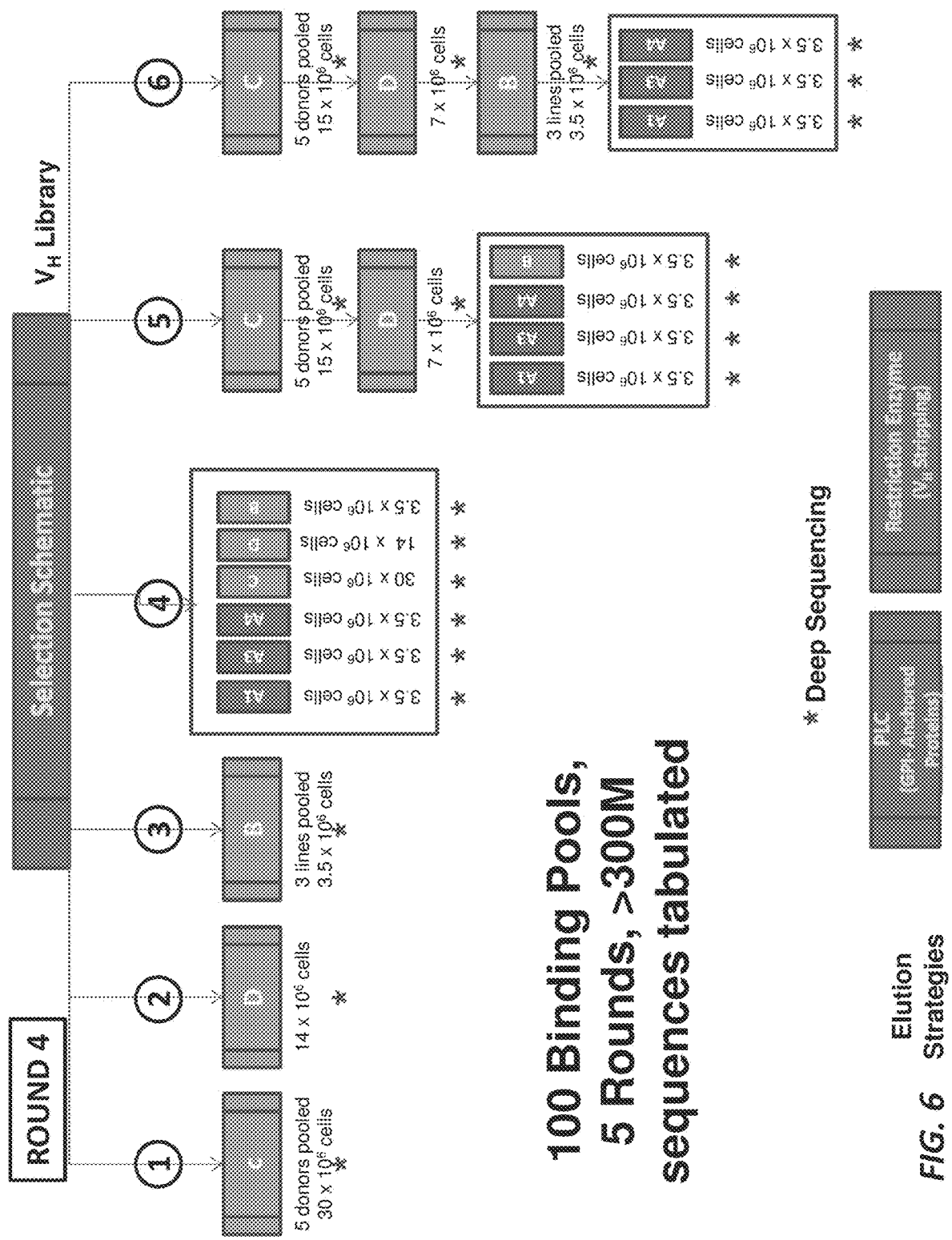
FIG. 6 is a schematic of exemplary parallel selection and deep sequencing strategies employed in the methods of the invention.

Identification of Target Cell Specific Epitopes Using Human VH Library and dsDNA Display Technology Incorporating Live Cell Selection and Deep Sequencing Analysis A. Summary A fully human antibody VH library obtained from bone marrow, peripheral blood and splenocytes of human donors was constructed and numerous high affinity and specific VH binders to multiple targets were identified using dsDNA display technology. Target cell specific epitopes were identified by live cell selection and deep sequencing analysis using human VH library and dsDNA display technology. Strategies of parallel, differential selections and target cell selective selections were applied in these methods (see FIGS. 4, 5, 6). The tabulation of the CDR3 frequency from deep sequencing of all pools across all rounds predicted the selectivity of the VH clones. High affinity VHs were identified that selectively bind to target cells and related cell types.

B. Library Engineering and Selection Methods for Live Cell Epitope Discovery

Two methods were developed to effectively recover library members that bound to live cells.

The first method involved stripping off binders from live cells by restriction digestion of the DNA fused to bound antibodies. This method enables the full recovery of the VHs bound to all epitopes on cells. A C-terminal of VH DNA library was engineered to carry a NotI restriction site (see FIG. 1). There are no NotI sites in naïve VH frameworks and therefore only full length VH binders are eluted from cells for subsequent amplification. The NotI restriction digestion buffer was tested on live cells, and with up to a 2 hour incubation at 37C the cells were viable. The efficiency of the NotI digestion was high. Following the binding of the library to cells for 1 hour at 4C, the cells were washed and digested with NotI buffer at 37C for 1 hour, the cells were then spun down, supernatant (containing bound VH DNA) was collected for PCR amplification (see FIG. 1).

Figure 2:
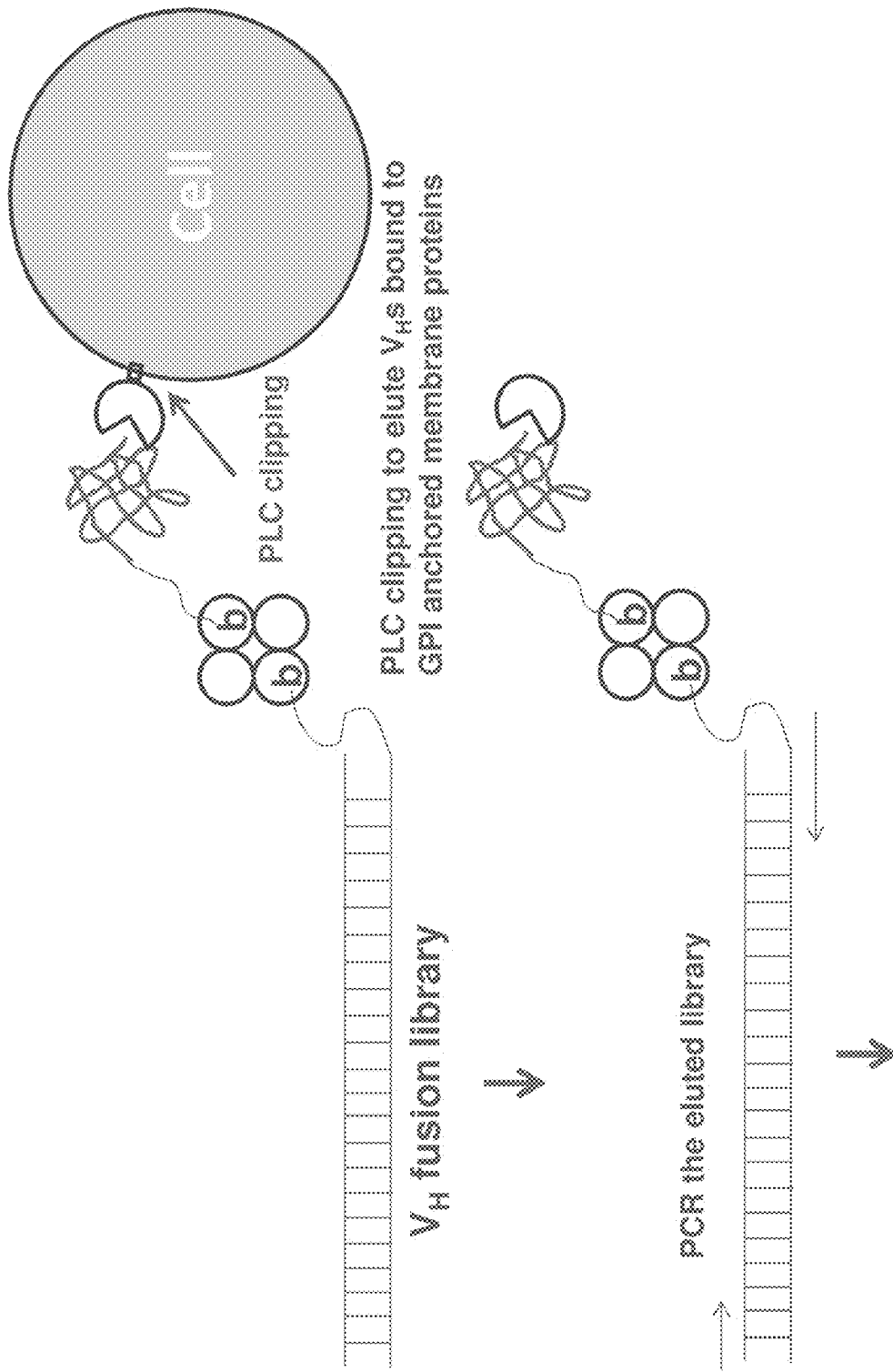
FIG. 2 is a schematic of exemplary DNA display compositions and screening methods of the invention.
Figure 3:
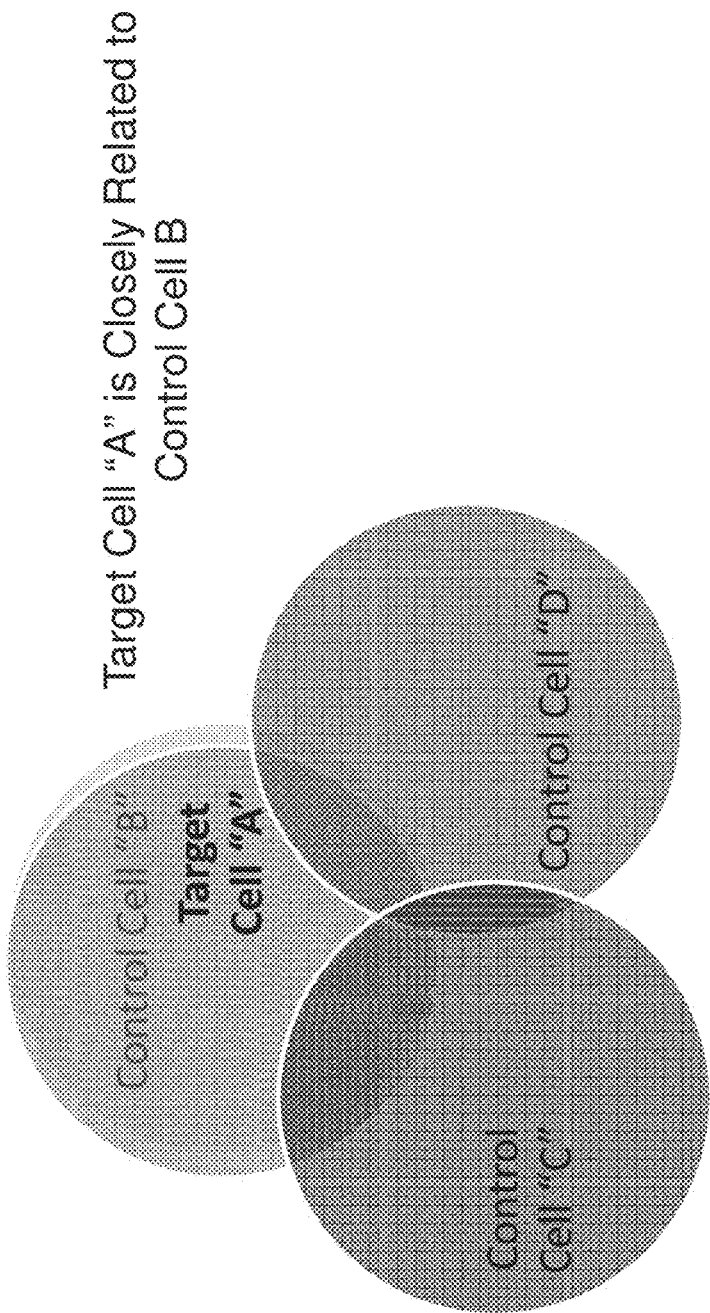
FIG. 3 is a schematic of exemplary target cell screening strategies employed in the methods of the invention.

The second method is to clip off VH binders from live cells using phospholipase C (PLC) digestion. This method enables the elution of the VHs that bound to the epitopes of any GPI anchored membrane protein (i.e., a subset of epitopes). The PLC clipping efficiency is high, as validated on FACS with control molecule. After incubation of library with cells for 1 hour at 4C, the cells were washed and incubated with PLC at 37C for 15 mins. The cells were subsequently spun down and the supernatant, containing fusion VH complexed with extracellular domain of the GPI anchored membrane protein, was PCR amplified (see FIG. 2).

C. Parallel Selections, Differential Selections and Target Cell Selective Selections on Target and Related/Undesired Cell Types Master naïve fusion library was produced according to the protocol set forth in WO2010/011944 (which is hereby incorporated by reference in its entirety). For first round of selection, the purified fusion library was split equally into multiple libraries that carry the same diversity for all selection branches (see FIG. 5).

Primary cells, obtained from normal donors or patients, were either thawed fresh or isolated from cell culture flasks, following standard cell biology protocols. The cells were then recovered for 1 hour in full media at 37C followed by blocking in selection buffer for 30 mins on ice. All the selections were carried out on ice to prevent antibody and target internalization.

For parallel selections, libraries were pre-cleared with 200 ul of pre-blocked streptavidin beads and 200 ul of pre-blocked hIgG-Epoxy beads for 30 mins at room temperature sequentially to remove any misfold and sticky library members. The pre-cleared libraries were then chilled on ice and subjected to pre-blocked cells and incubated on ice for 1 hour.

For target cell selective selections, pre-clearance was performed on undesired and closely related cell types for 1 hour on ice to remove any non-selective binders and then subjected on target cells.

At selection round 4, differential selection methods were applied to the branches of selection on target cells (with and without pre-clearance on cells). In this round, libraries were split into multiple tubes and bound to each cell type and patient's cells from different stage of the diseases in parallel. This strategy allowed for direct comparison of target cells versus other cell types by deep sequencing analysis and identification of binders recognizing different epitopes that arose with disease progression (see FIG. 6).

For all selection branches, after binding, cells were washed with 10 mL of binding buffer and subject to either NotI restriction digestion to recover all binders to membrane protein or PLC clipping to recover binders to GPI anchored membrane proteins as described above.

D. Deep Sequencing Analysis to Predict Selective Binders to Target Cells

After each round of selection, binding pools were PCR amplified. The HCDR3 of each binding pool was lifted up by PCR with oligos priming C-terminal of framework 3 and N-terminal of framework 4 of VH fragments. These HCDR3 fragments derived from individual selection rounds and branches were then tagged with specific DNA bar code used for Illumina sequencing by PCR. The tagged HCDR3 were pooled and sent for high throughput sequencing with Hi Seq technology. The round 4 binding pools from target cells were also tagged with DNA bar code and submitted for 454 sequencing to get full length VH sequences.

Figure 7:
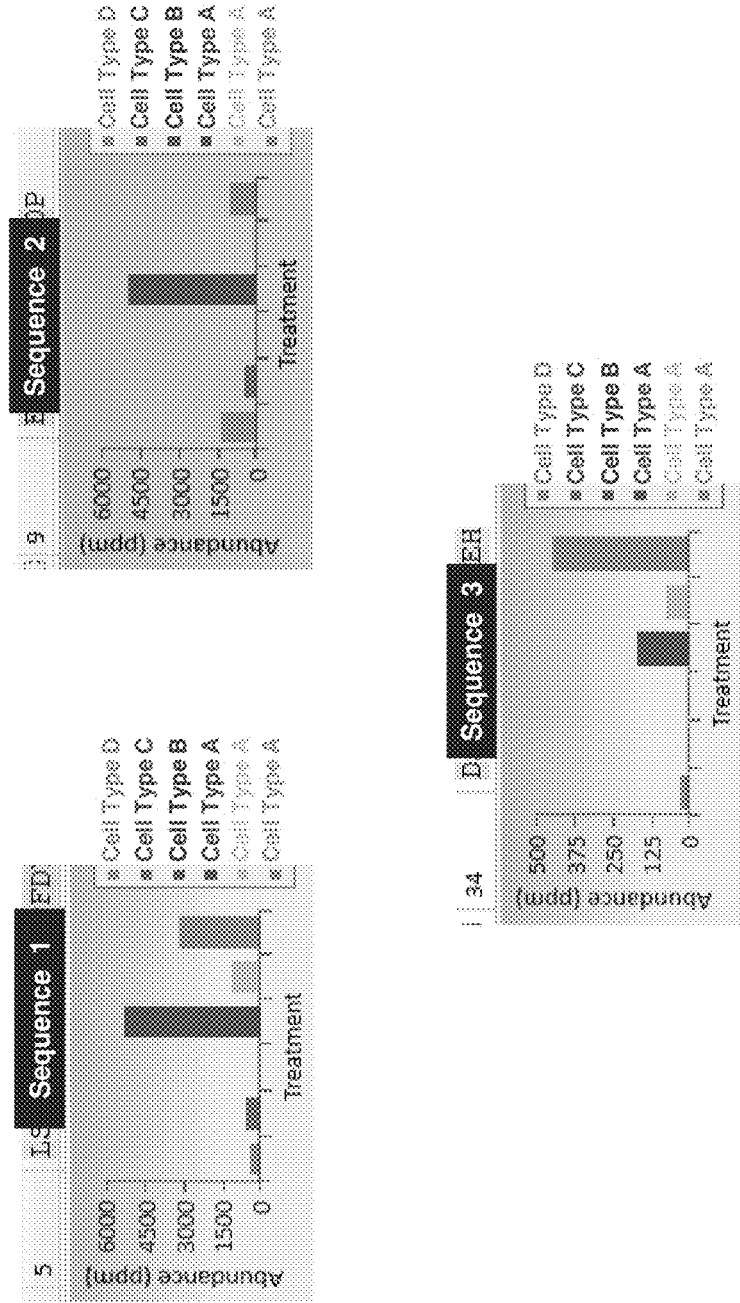
FIG. 7 is a schematic of the results of exemplary parallel selection strategies and deep sequencing analysis employed in the methods of the invention.

The sequences were deconvoluted based on the DNA bar code after sequencing. Millions of sequences derived from each selection round and selection branch were tabulated by comparing the frequency of a particular CDR3 sequence present at different rounds and selection branches. The criteria used for identification of selective binders were: 1) specific enrichment of a CDR3 sequence from earlier round to later round on target cells, not on control or close related cell types; 2) higher frequency on target specific cell type and low on control or closely related cell type at differential selection round (see FIG. 7); and 3) sequences not present in other target or cell selections from other programs in database. The selective clones identified by Illumina sequencing were then synthesized based on the 454 full length sequence information.

E. Production, Purification and FACS Binding Assays

Figure 8:
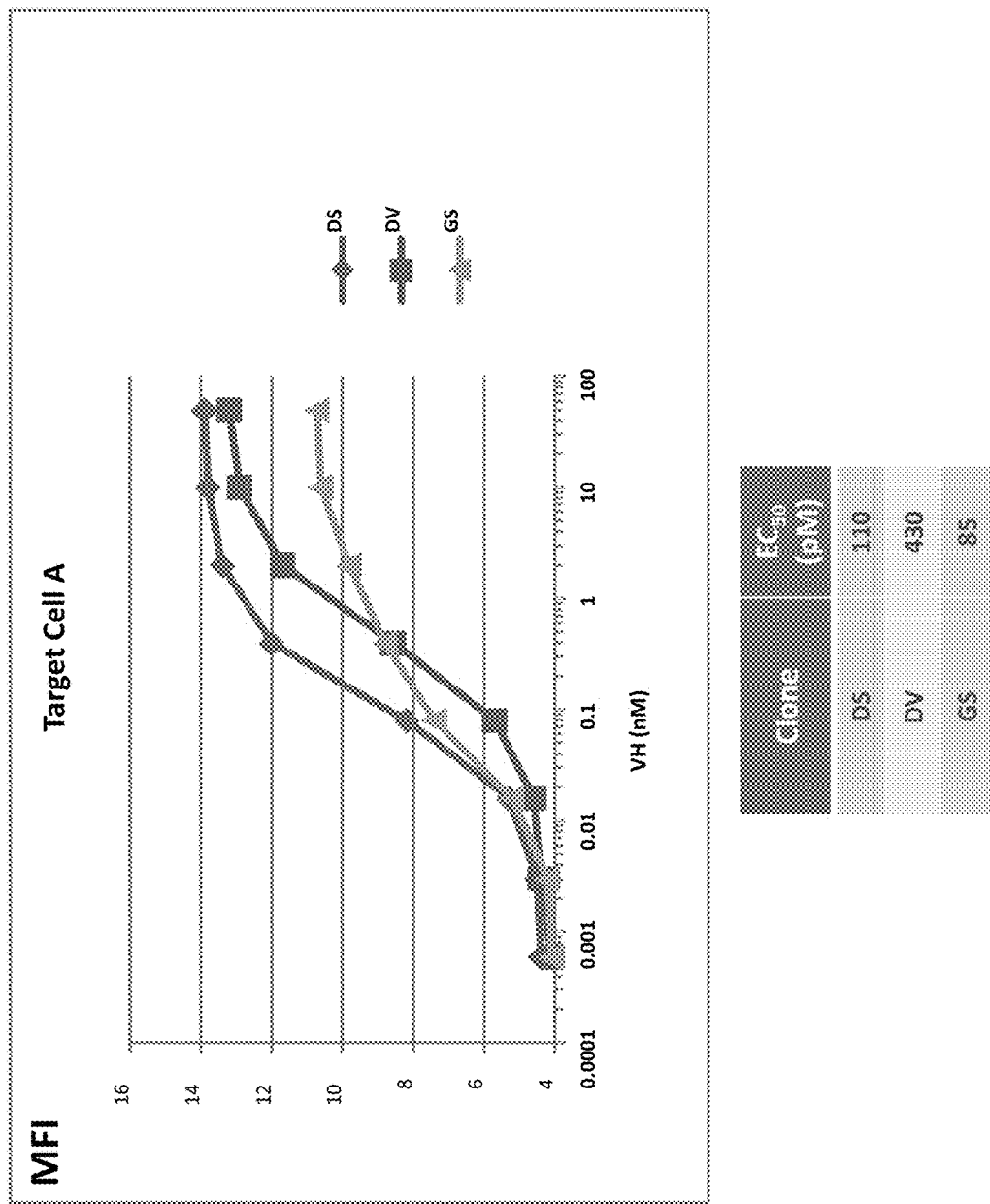
FIG. 8 depicts a graph showing the results of a FACS based binding assay of high affinity VH molecules selected using the methods of the invention.
Figure 9:
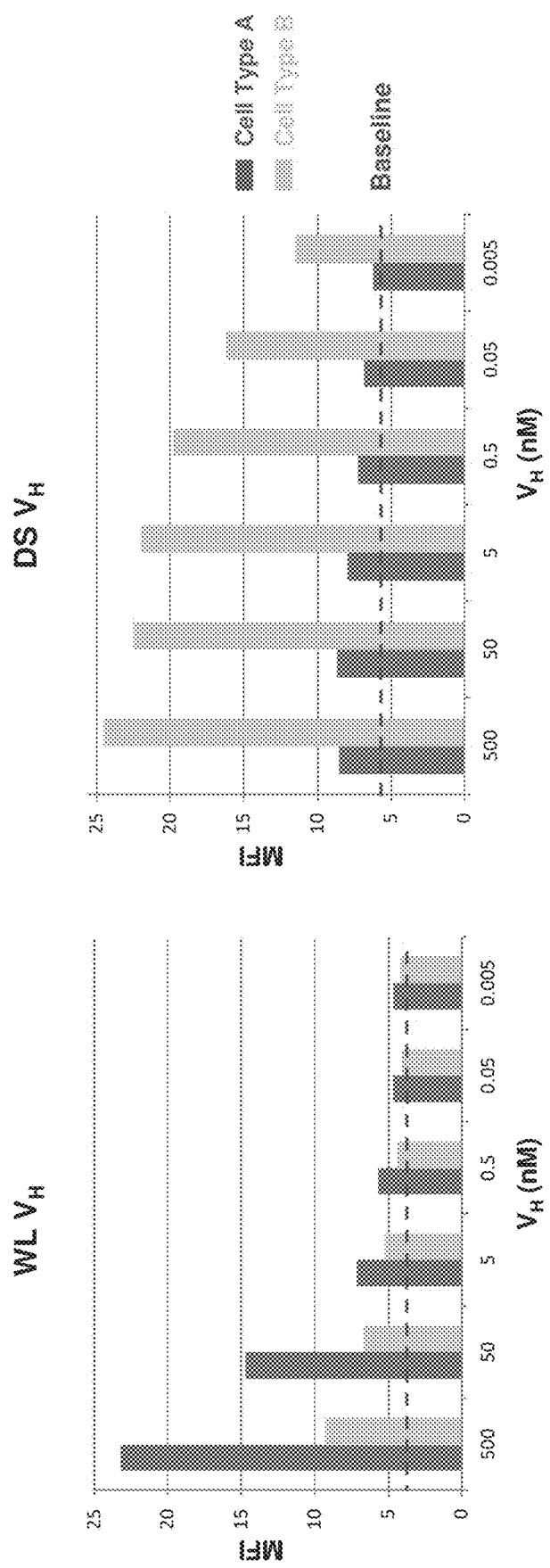
FIG. 9 depicts graphs showing the differential binding of VH molecules selected using the methods of the invention.
Figure 10:
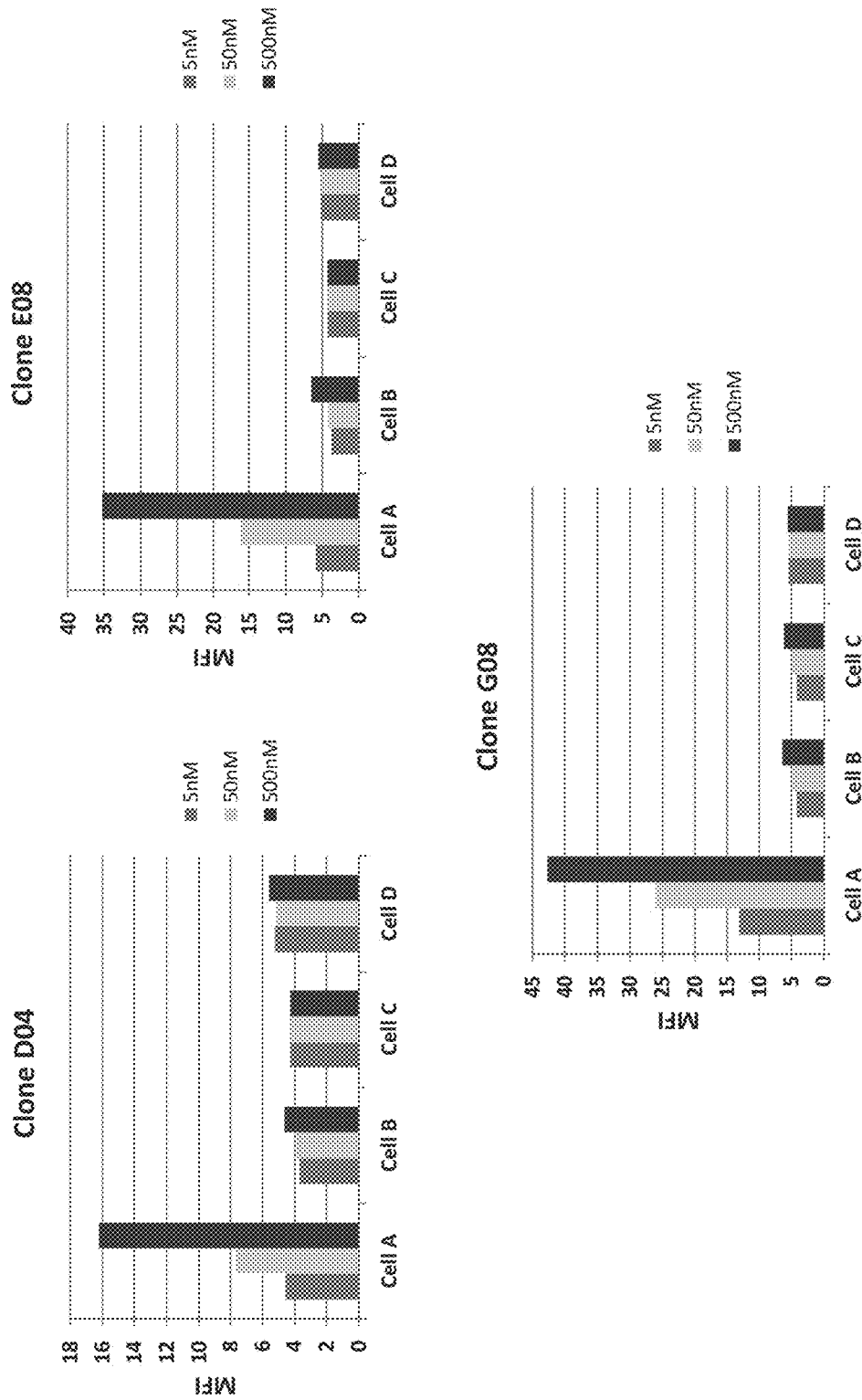
FIG. 10 depicts graphs showing the differential binding of VH molecules selected using the methods of the invention.
Figure 11:
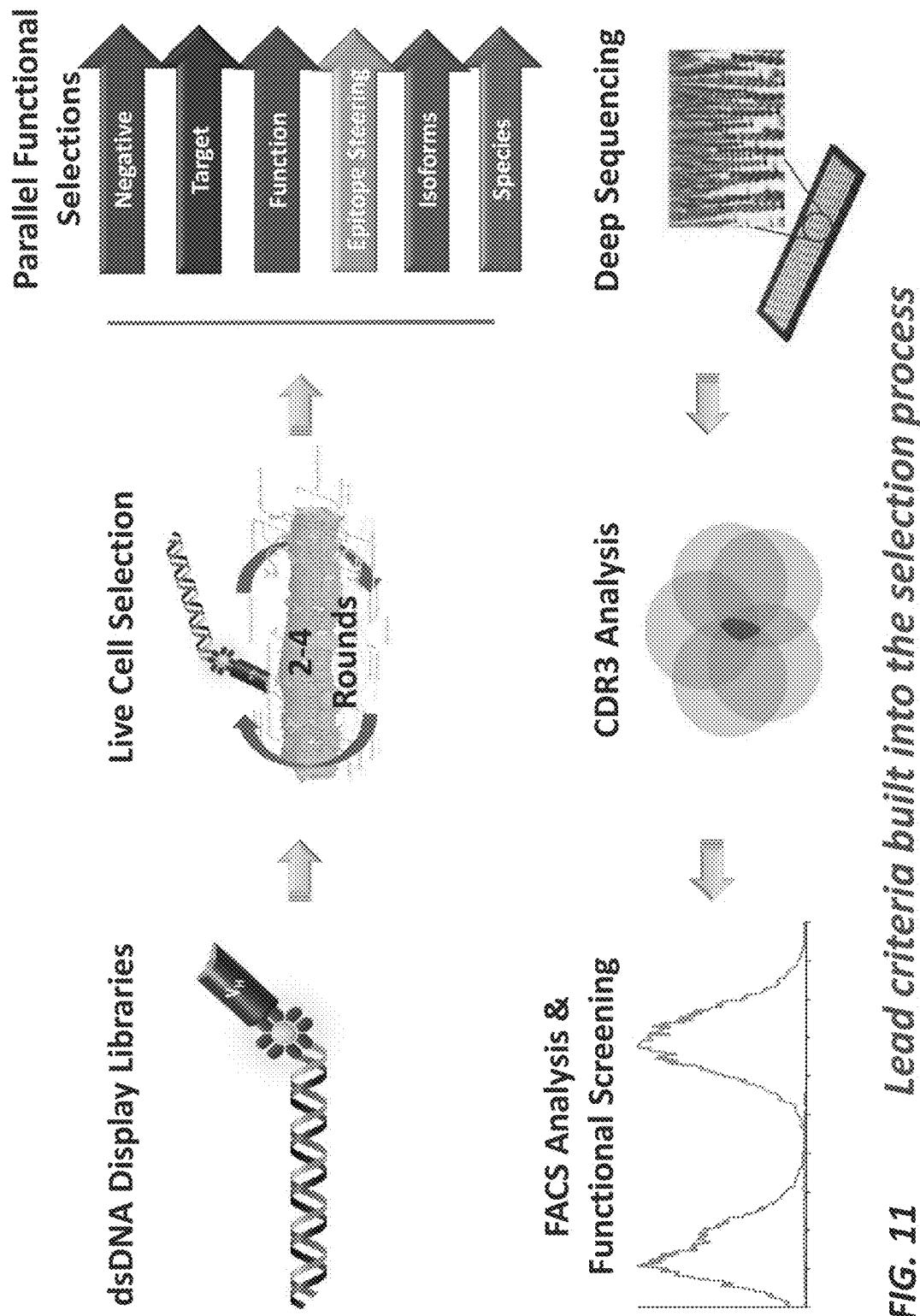
FIG. 11 is a schematic of exemplary parallel screening and deep sequencing strategies employed in the methods of the invention, in which iterative rounds of live cell selection with parallel functional selective pressures are applied to enrich for antibodies that bind to and modulate specific cell surface proteins. Selected pools are bar-tagged and subjected to deep sequencing. The comparative bioinformatic analysis of enriched sequences from parallel selections allows for the identification of antibodies that possess selectivity and activity matching lead criteria.
Figure 12:
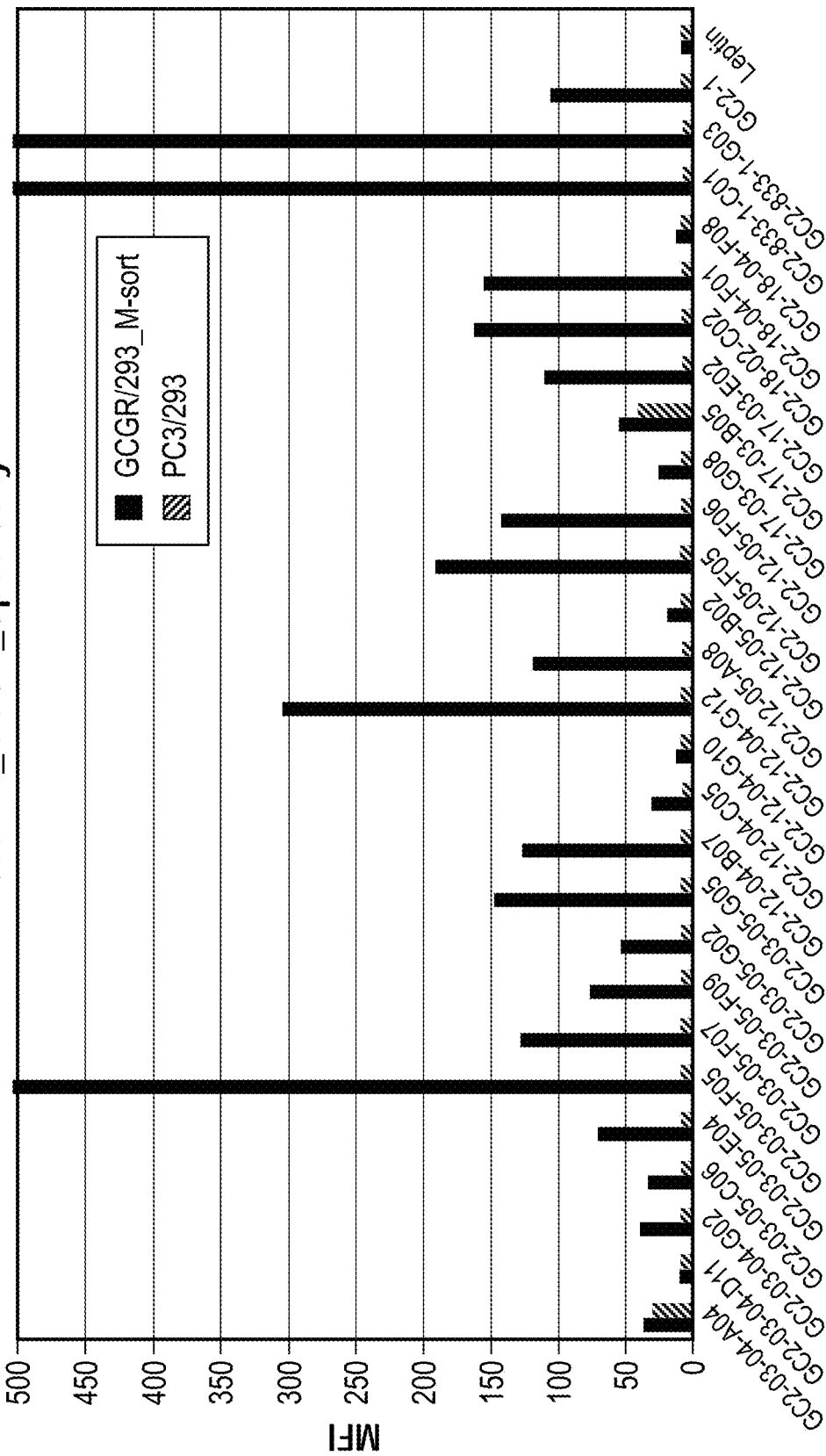
FIG. 12 depicts the results of exemplary parallel screening strategies using the methods disclosed herein to identify anti-glucagon receptor (GCGR) VH domains. Enriched pools from live cell GCGR (a class B GPCR) selections were subjected to binding and functional assays, including (counter-clockwise) competitive binding, cAMP, label-free adhesion, cellular internalization, and b-arrestin assays. A diverse set of activity-modulating anti-GCGR VH domains were isolated which exhibited distinct functional activities through several different mechanism of action.
Figure 12:
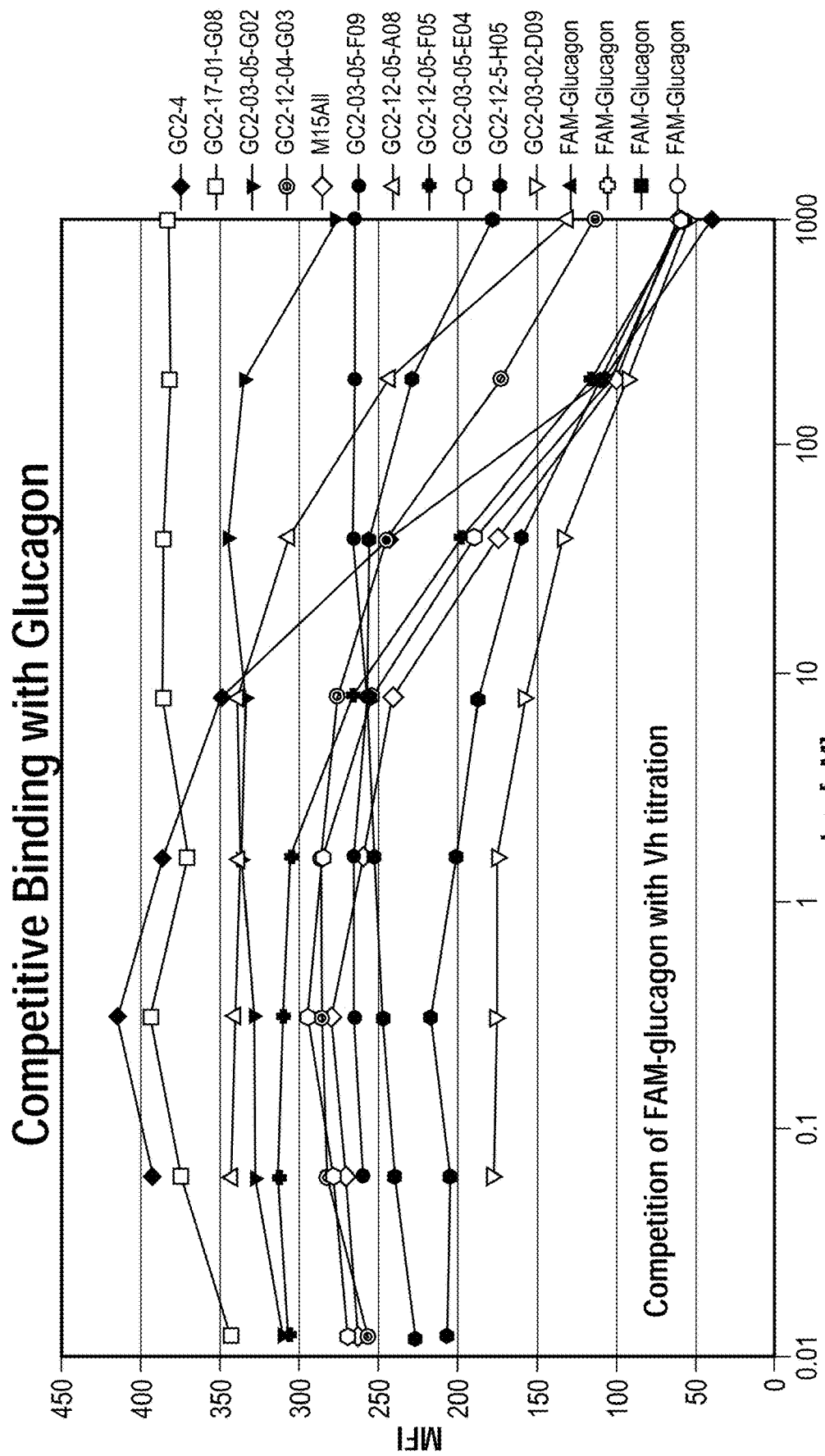
Figure 12:
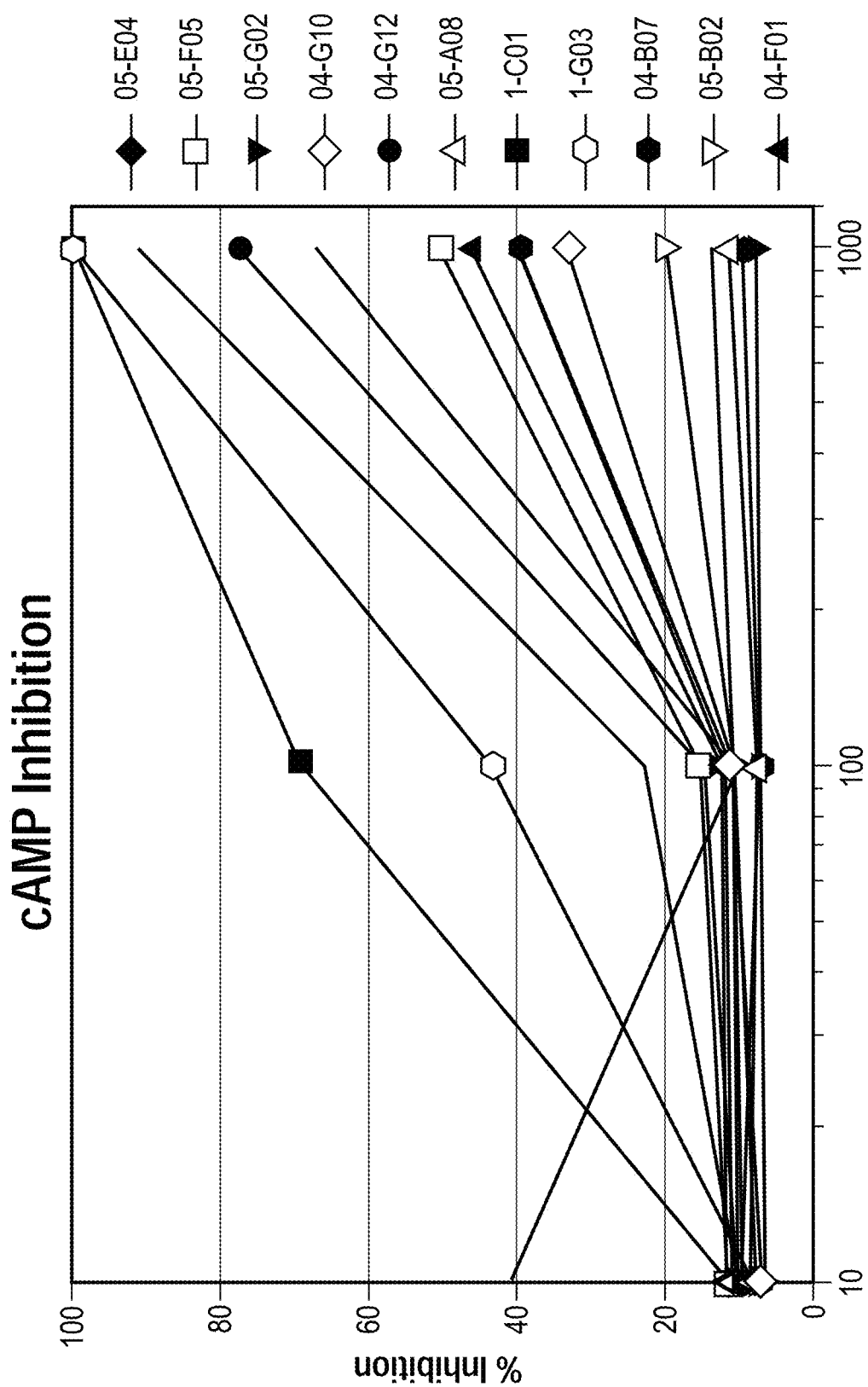
Figure 12:
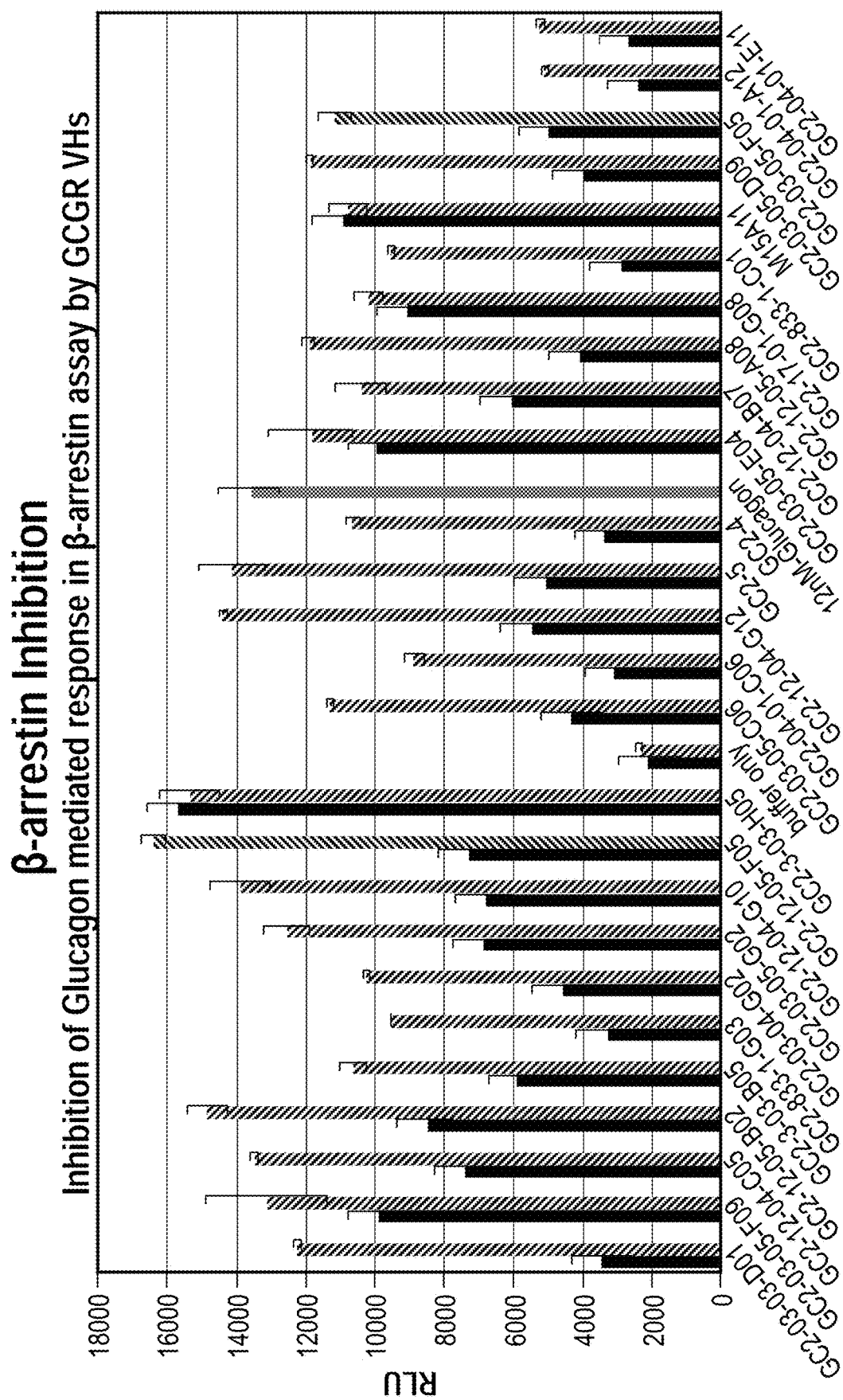
Figure 12:
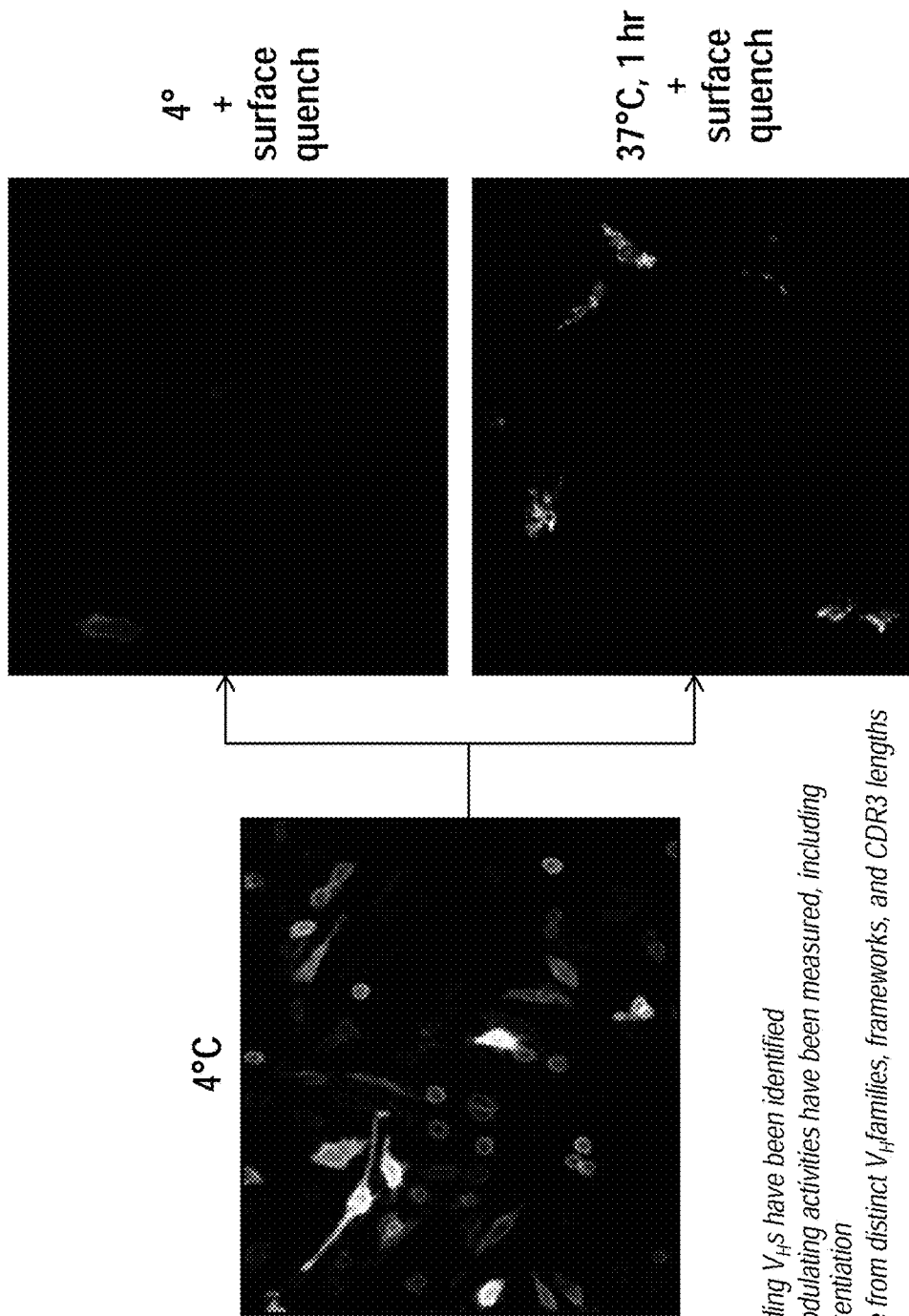
Figure 12:
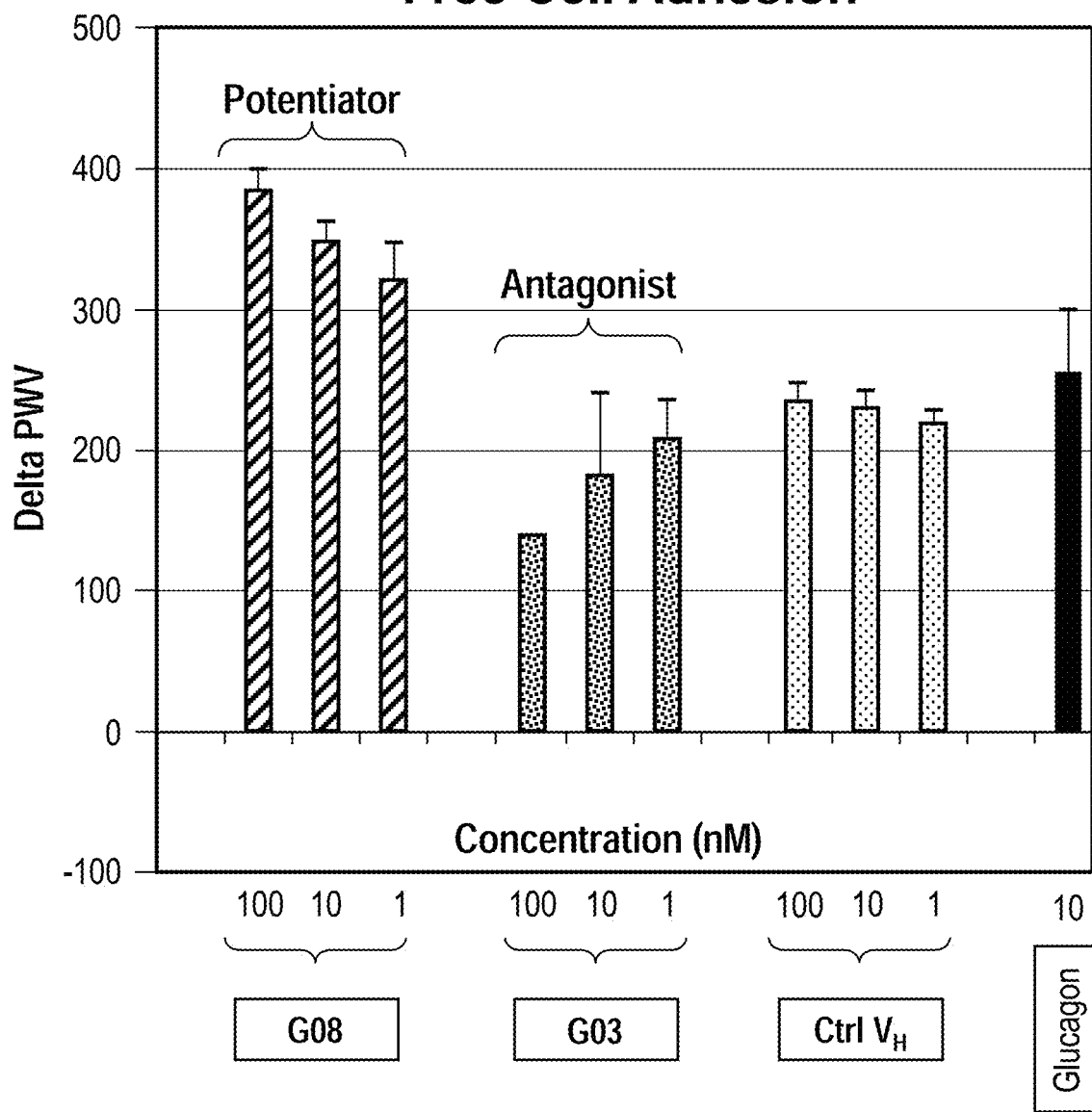
Figure 13:
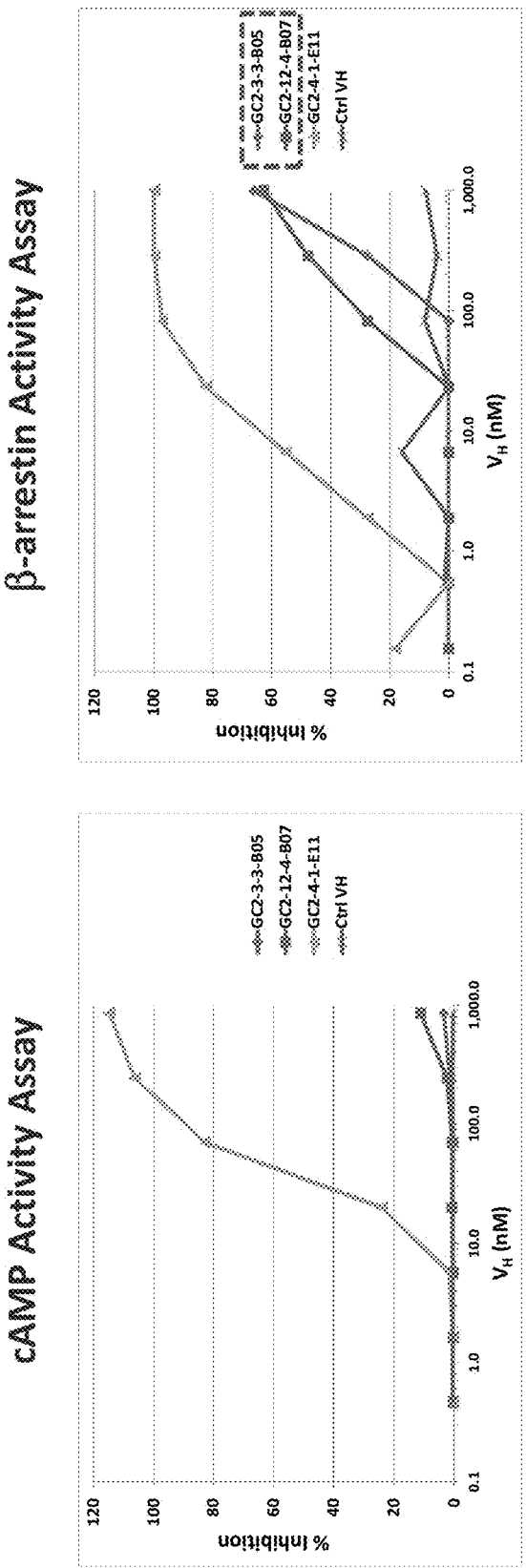
FIG. 13 depicts the results of cAMP and b-arrestin assays of anti-GCGR VH domains selected using the methods disclosed herein. HEK293 cells expressing GCGR were challenged with 10 nM glucagon in the presence or absence of the indicated VH domains. Clones B07 and B05 inhibit GCGR induced b-arrestin activity but have little effect on receptor-activated cAMP production.
Figure 14:
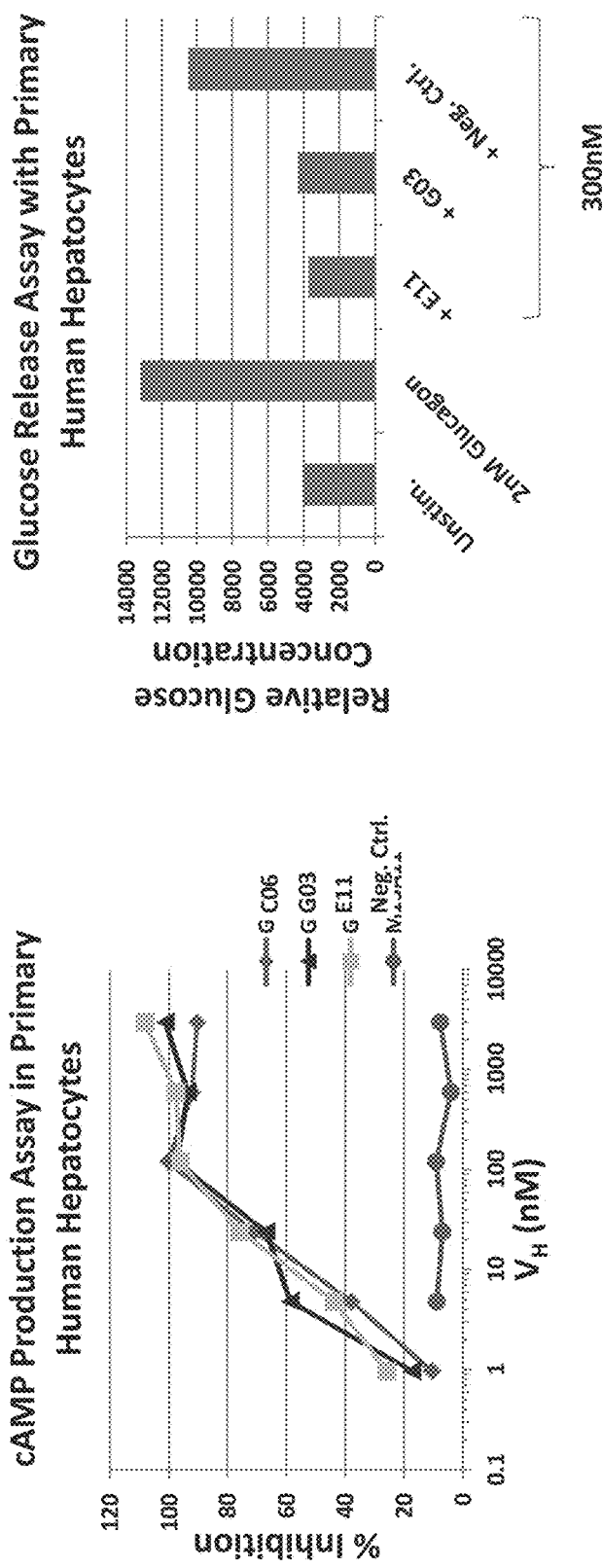
FIG. 14 depicts the results of cAMP and glucose release assays of anti-GCGR VH domains selected using the methods disclosed herein. Primary human hepatocytes were stimulated with 2 nM glucagon in the absence or presence of the indicated GCGR VH domains. Both glucagon-activated cAMP production and glucose release are inhibited by the VH domains, demonstrating the functional activity of these clones against endogenous receptor and in biologically relevant assays
Figure 15:
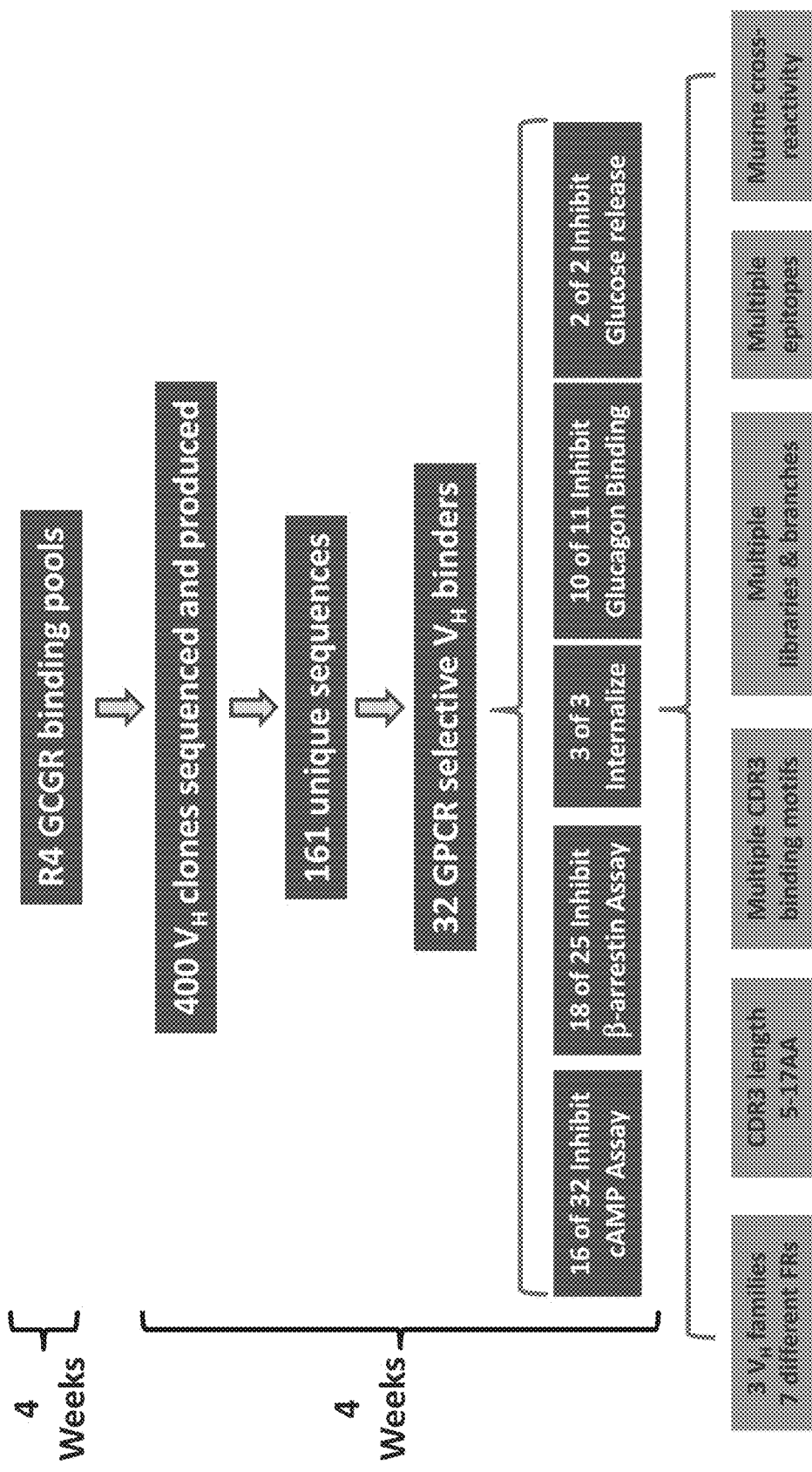
FIG. 15 is a schematic of an exemplary parallel live cell selection identifying anti-GCGR VH domains with a variety of diversity and functional characteristics.
Figure 16:
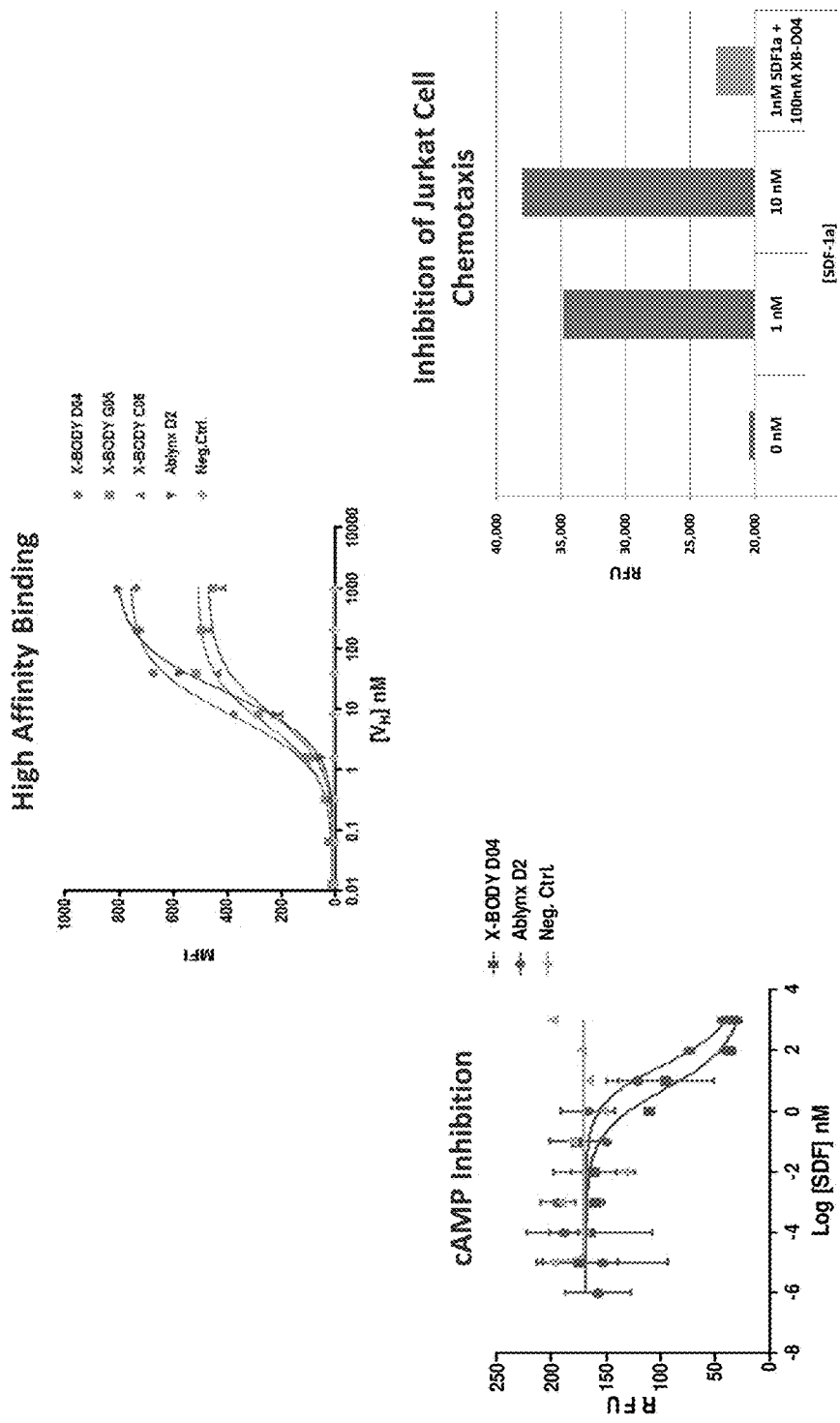
FIG. 16 depicts the results of binding, cAMP and chemotaxis assays of anti-CXCR4 VH domains selected using the methods disclosed herein. Live cell functional selections against CXCR4 (Class A chemokine GPCR) yielded a diverse set of VH domains that demonstrate specific binding to CXCR4-expressing cells, inhibition of SDF-1a-mediated cAMP signaling, and inhibition of ligand-induced chemotaxis in Jurkat cells with endogenously expressed CXCR4.
Figure 17:
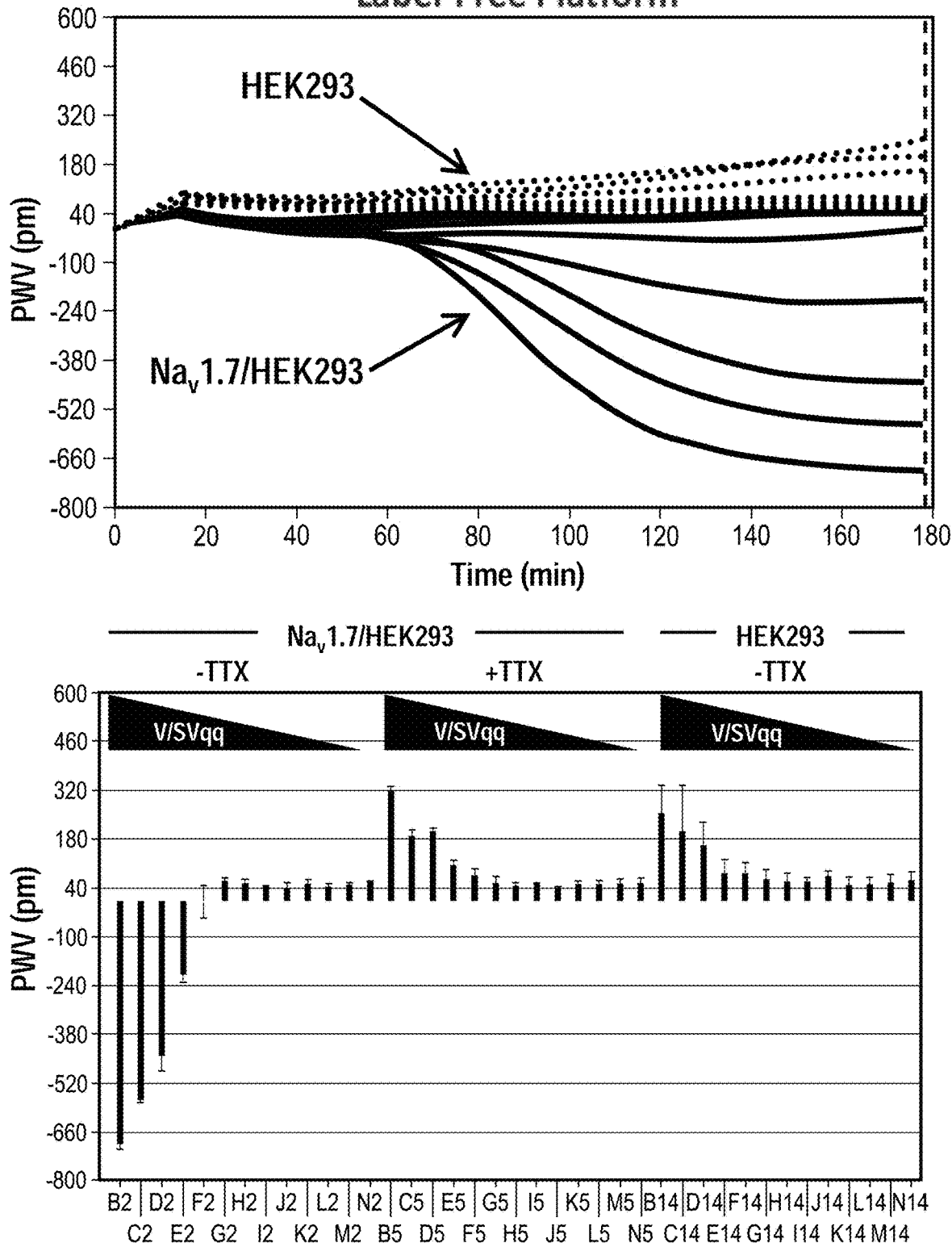
FIG. 17 depicts the results of BIND label-free cellular response assays of HEK293 cells expressing Nav1.7 stimulated with veratridine and scorpion venom. BIND allows for real-time, label-free cellular response measurements by monitoring changes in peak wavelength values (PWV) of reflected light from the surface of optical biosensors. Recombinant Nav1.7/HEK293 cells were stimulated with veratridine (V)+scorpion venom (SVqq) to activate channels. BIND measured a delayed secondary response to channel opening that elicited a decrease in PWV after 1 hour post-stimulation. Tetrodotoxin (TTX) inhibited Nav1.7 channels and reversed the negative PWV shift to a response observed in parental HEK293 cells.

The binding pools and synthesized VHs were then sub-cloned into pET22b expression vectors. The VHs were produced in BL-21 *E. coli* cells and purified through C-terminal His tag using standard protocols. FACS assay was performed to assess the binding and selectivity of VHs to different cell types and the EC50 of the binders. High affinity and selective VH binders were identified through the live cell selection process (see FIGS. 8, 9 and 10).

EXAMPLE 2

Enhanced Diversity VH Library Construction

To expand the diversity of existing VH naïve libraries (e.g., those disclosed in WO2010/011944), a CDR3 and framework reshuffling approach was adopted. Briefly, PCR was performed using oligos priming the C terminal region of VH framework 3 and the N terminal region of framework 4. This strategy was designed to amplify the entire CDR3 loop domain from each of the VH families derived from naïve VH libraries. VH frameworks 1-3 were amplified by PCR with family-specific degenerate N-terminal framework 1 and C-terminal framework 3 oligos from the same naïve library. Overlapping PCR was performed using T7 UTR and framework 4 oligos with CDR3 and frameworks mixed at equal molar ratio. The reshuffled library was further modified to carry the purification tags for dsDNA fusion library for selections. Specifically, the HCDR3 from the naïve library was lifted up from each $V_H$ family with framework 3 and framework 4 forward and reverse oligos and assembled into a library comprising framework regions 1-3 of naïve human $V_H$ domains amplified from bone marrow B cells and PBMCs using framework specific oligonucleotides. Human VH framework regions 1-3 were amplified using 5' VH family-specific and 3' generic FR3 reverse primers to create separate libraries of VH family framework regions. The VH family framework libraries and the HCDR3 lifted from the same library were shuffled by further PCR amplification using 5' T7TMV and 3' FR4 oligos. This also added a T7TMV promoter sequence at the 5' end for in vitro transcription/translation. A C-terminal CO sequence and a FLAG tag (for purification after translation) were also added by PCR using FR4 Cμ3 Reverse and Y109 primers, respectively, together with the 5' T7TMV primer. The nucleic acid sequences of the oligonucleotides used for preparation of the HCDR3-shuffled VH library are set forth in Table 1.

Library diversity can be further enhanced by expanding to include more donors from normal individuals and disease patients, if desired.

TABLE 1

Oligonucleotides for constructing HCDR3 shuffled VH libraries

| Oligo | Sequence | SEQ ID NO. |
|---|---|---|
| FR3 Reverse | CGCACAGTAATACACGGC | 1. |
| VH1a | CAATTACTATTTACAATTACAATGCAG GTKCAGCTGGTGCAGTCTG | 2. |
| VH1b | CAATTACTATTTACAATTACAATGCAG GTCCAGCTTGTGCAGTCTG | 3. |
| VH1c | CAATTACTATTTACAATTACAATGSAG GTCCAGCTGGTACAGTCTG | 4. |
| VH1d | CAATTACTATTTACAATTACAATGCAR ATGCAGCTGGTGCAGTCTG | 5. |
| VH2 | CAATTACTATTTACAATTACAATGCAG RTCACCTTGAAGGAGTCTG | 6. |
| VH3a | CAATTACTATTTACAATTACAATGGAR GTGCAGCTGGTGGAGTCTG | 7. |
| VH3b | CAATTACTATTTACAATTACAATGCAG GTGCAGCTGGTGGAGTCTG | 8. |
| VH3c | CAATTACTATTTACAATTACAATGGAG GTGCAGCTGTTGGAGTCTG | 9. |
| VH4a | CAATTACTATTTACAATTACAATGCAG STGCAGCTGCAGGAG | 10. |
| VH4b | CAATTACTATTTACAATTACAATGCAG GTGCAGCTACAGCAGTGG | 11. |
| VH5 | CAATTACTATTTACAATTACAATGGAR GTGCAGCTGGTGCAGTCTG | 12. |
| VH6 | CAATTACTATTTACAATTACAATGCAG GTACAGCTGCAGCAGTCAG | 13. |
| VH7 | CAATTACTATTTACAATTACAATGCAG GTGCAGCTGGTGCAATCTG | 14. |
| T7TMVUTR | TAATACGACTCACTATAGGGACAATTA CTATTTACAATTACA | 15. |
| FR3 Forward | GCCGTGTATTACTGTGC | 16. |
| FR4 Cu3 Reverse | GGAGACGAGGGGGAAAAGGGTTGAGGA GACGGTGACCAG | 17. |
| Y109 | TTTTTTTTTTTTTTTTTTTAAATAGC GGATGCTAAGGACGACTTGTCGTCGTC GTCCTTGTAGTCGGAGACGAGGGGGAA AAGGGT | 18. |

The enhanced diversity library can be further engineered for live cell surface stripping selection methodology, as described in herein.

EXAMPLE 3

Live Cell Selection Using Human VH Library and dsDNA Display Technology Incorporating by Immunoprecipitation Various surfactants were evaluated for the ability to solubilize GPCRs and still preserve native functional conformations. Specifically, a $^{35}$S labeled antibody binding assay was developed using control a VH molecule (including a Myc affinity tag) and a GPCR-expressing cell line. In this assay, equal numbers of GPCR target-expressing cells were lysed with Triton X100, CHAPS, DDM or Brij35 surfactants, followed by immunoprecipitation with anti-Myc tag antibody and capture by Protein G magnetic beads. A positive control VH that binds to the target cells was radio labeled with $^{35}$S during the in vitro translation reaction. The labeled VH was incubated with GPCR target, and captured by anti-Myc antibody following cell lysis with the different surfactants described above. The amount of VH bound to the GPCR target was quantified using a scintillation counter. The functional conformation preserved by the surfactant solubilization was ranked based upon the VH binding activity. In parallel, the quantity of GPCR immunoprecipitated with anti-Myc antibody was evaluated by Western blot. The positive control VH showed better activity binding to GPCR when cells were lysed with DDM or CHAPS. The combination of DDM and CHAPS showed maximum functional GPCR activity and optimal GPCR quantity in these two assays and was selected for use in selections for GCGR (Glucagon receptor)-binding VH domains.

In one GCGR selection branch, purified and pre-cleared VH DNA-display library was contacted with GCGR-expressing cells for 1 hour. The cells were washed and lysed with DDM/CHAPS, followed by immunoprecipitation with anti-Myc tag antibody. The VH-GCGR-Myc Ab complex was recovered and VH DNA eluted using 0.1N KOH. Using this method, high affinity VH that bind to GCGR-expressing cells were identified after 4 rounds of selections.

Alternatively, the selections can be performed using solubilized and concentrated GPCR target (or another target of interest) that has been immunoprecipitated with anti-Myc antibody after solubilization of cells with DDM/CHAPS. The VH library can then be eluted following incubation with these targets captured on beads.

In addition to the methods described above, upon VH library binding to live cells expressing functional GPCRs (or other target of interest), the cells can be lysed and immunoprecipitated with anti-intracellular N or C-terminal antibodies similar to anti-Myc antibody. Anti-phosphorylation-specific antibodies can be applied to capture activated receptors and segregate from inactivated receptors. Immunoprecipitation can also be performed with antibodies to the accessory molecules that associate with activated or inactivated targets to capture VHs that modulate various activating and inactivating states of target specific pathways. The DNA display library members in these binding pools can then be tagged with DNA bar codes during PCR amplification and submitted for deep sequencing to identify functional binders with different mechanisms of action.

EXAMPLE 4

Internalization Selection

A selection methodology was developed to identify agonist or antagonist antibodies with internalization activity. Briefly, a naïve human dsDNA display VH library (as described above) was incubated at 37° C. with live cells expressing a GPCR (or other target of interest) in the presence of 50 mM $NH_4Cl$, to allow for GPCR-binding VH to internalize. The cells were then washed was buffer and the cell surface VH were stripped off by low pH acid (e.g., 0.1M HCL, pH 2.7). After low pH stripping, the cells were lysed with a combination of CHAPS/DDM, as described above, and precipitation of DNA was performed to recover the coding sequences of the internalized dsDNA display library members. Alternatively, immunoprecipitation with anti-c-terminal or anti-Myc tag antibody can be performed. Both of these methods can also be combined. For example, in a selection for GCGR-binding VH, four rounds of screening were performed in which internalized library members were recovered by DNA precipitation, followed by a fifth round of screening where immunoprecipitation of the internalized library members with an anti-Myc antibody was applied to increase the selective stringency. In these experiments, high affinity antagonists were identified after five rounds of internalization selections. These GCGR-binding VH demonstrated internalization activity consistent with the selective pressure applied.

EXAMPLE 5

Live Cell Selections on Activated/Deactivated State of the Target Cells

To enhance the targeting functional epitopes of GPCR targets and the identification of allosteric, modulatory VH, selection strategies were developed to allow selections on activated and deactivated target cells (e.g., agonist-activated or antagonist-inactivated GPCR in live cells). Selections in the presence of the endogenous ligand (or aligand-analog) favors the identification of VH that bind to positions distinct from the orthosteric binding site or to novel epitopes presented by both ligand and receptor. Briefly, GCGR-expressing cells were blocked and incubated with a naïve human dsDNA display VH library (as described above) in the presence of agonist (ligand, analog or agonistic antibodies) or antagonist (inhibitors or neutralizing antibodies). For example, in selections against GCGR, one selection branch was performed in the presence of glucagon. In another GPCR selection, some selection branches were performed in the presence of a ligand mimetic, and antagonist, to identify allosteric modulators. These selections with activated and deactivated target cells were coupled with the various library recovery methods disclosed herein for effective capture of VH that bind to GPCR targets in the desired activation state.

EXAMPLE 6

Ligand Elution and Epitope Steering on Live Cells to Identify Orthosteric and Allosteric Modulators of GPCRs Methods were developed for targeting specific functional epitopes of GPCRs (or other targets of interest) using live cell selections. These methods allow for the identification of orthosteric (agonist/antagonist) and allosteric modulators of GPCRs. For example, in a selection for GCGR-binding VH, one branch of selection was performed in the presence of glucagon. For another branch of the GCGR selection, after antibody library was incubated with GCGR-expressing target cells, the cells were washed and eluted with glucagon for four hours. The remaining binders that bound to epitopes distinct from the ligand binding domain was then stripped off from cells using the methods disclosed herein. From these experiments, several high affinity VH domains were identified that block glucagon binding to, and ligand induced cAMP induction by, GCGR. One of the identified VH domains functioned as a positive allosteric modulator. For another target, we have used antagonist antibodies to pre-block the epitope on cells selected in the presence of the antagonist antibody. This experiment resulted in the identification of multiple VH domains that recognize distinct epitopes from the existing antagonist reference antibodies.

EXAMPLE 7

Selectivity for Rodents, Primates, Homology Membrane Proteins

To increase the selectivity of anti-GPCR antibodies for GPCR species homologs, cell lines expressing these related homologs can be generated in parallel and utilized in the DNA-display selection processes described herein, either as counter selection tools (if cross-species is not desired) or used in parallel with target cell selections, followed by deep sequencing and bioinformatics tabulation to identify selective clones. To generate antibodies that are cross-reactive with rodent or primate for subsequent animal efficacy and toxicity studies, selections were performed with an initial round of selection on human target cells, followed by cross over selections against rodent target-expressing cells. Alternatively, human and rodent cells can be used at alternate rounds of selection. Many of the VH domains identified demonstrated binding to both the human and the rodent target on cells, avoiding the need to generate surrogate antibodies for animal studies.

EXAMPLE 8

Application of Deep Sequencing

Deep sequencing technology has been applied extensively in the DNA-display selection processes described herein. In certain experiments, lead criteria were built into the selection process and many parallel selections were performed. HCDR3 fragments derived from individual selection rounds and branches were tagged with specific DNA bar codes used for Illumina sequencing by PCR. The tagged HCDR3 were pooled and sent for high throughput sequencing with Hi Seq or My Seq technology. The sequences were deconvoluted based on the DNA bar code after sequencing. Millions of sequences derived from each selection round and selection branch were tabulated by comparing the frequencies of a particular CDR3 sequence present at different rounds and selection branches to guide the selection of lead molecules with selective binding, epitope coverage and functional profiles incorporated.

We claim:

1. A method of identifying a binding polypeptide that specifically binds to a cell-surface antigen, the method comprising:

(a) contacting a cell, that naturally expresses a cell-surface antigen on its exterior surface, with a variegated DNA-display library of binding polypeptides, thereby forming a binding polypeptide/antigen complex, wherein the contacting of the cell with the DNA-display library is performed in suspension under conditions whereby the complex remains on the cell surface or is internalized;

(b) washing unbound library members from the cell;

(c) isolating at least one binding polypeptide/antigen complex; and (d) separating the at least one bound library member from the cell-surface antigen, thereby identifying a binding polypeptide that specifically binds to the cell-surface antigen.

2. The method of claim 1, wherein the method further comprises washing the cell with a low pH solution to remove library members that remain bound to the exterior surface after step (b).

3. The method of claim 2, wherein the contacting occurs under conditions that allow for internalization of the binding polypeptide/antigen complexes prior to step (b), and wherein the internalized binding polypeptide/antigen complexes are isolated using a binding agent specific for a portion of the binding polypeptide or the antigen.

4. The method of claim 1, wherein the variegated DNA-display library is a V-domain library, each member of the library comprising FR1-FR3 region sequences from a first antibody and CDR3-FR4 region sequences from a second antibody.

5. The method of claim 4, wherein the FR1-FR3 region sequences are from the naive immunological repertoire of a human.

6. The method of claim 4, wherein the CDR3-FR4 region sequences are from the naive immunological repertoire of a human.

7. The method of claim 1, wherein each member of the DNA-display library comprises a binding polypeptide linked through an intervening DNA linker to a DNA coding sequence encoding the binding polypeptide, wherein the DNA linker comprises a restriction endonuclease site not present in the coding sequence of members of the DNA-display library.

8. The method of claim 7, wherein separating the bound library member from the cell-surface antigen comprises enzymatically cleaving the restriction endonuclease site with the suitable restriction endonuclease to separate the DNA coding sequence from the binding polypeptide/antigen complex.

9. The method of claim 1, wherein the method further comprises determining the DNA coding sequence of at least a portion of the separated library members.

10. The method of claim 1, wherein the cell is a tumor cell.

11. The method of claim 1, wherein the binding polypeptide is an antibody or fragment thereof.

12. The method of claim 1, wherein the cell is a primary cell.

13. The method of claim 2, wherein the contacting occurs under conditions that allow for the binding polypeptide/antigen complexes to remain on the cell surface prior to washing the cell with a low pH solution, and the binding polypeptide/antigen complexes removed from the cell surface by the low pH solution are isolated using a binding agent specific for a portion of the binding polypeptide or the antigen.

14. The method of claim 2, wherein the low pH solution has a pH of less than about 5.0.

15. The method of claim 2, wherein the low pH solution has a pH of less than about 3.0.

16. The method of claim 15, wherein the low pH solution comprises HCl or glycine.

17. The method of claim 15, wherein the low pH solution comprises 0.1 M HCl.

\* \* \* \* \*

SEQUENCE LISTING

<160> NUMBER OF SEQ ID NOS: 28

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgcacagtaa tacacggc                                                      18

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caattactat ttacaattac aatgcaggtk cagctggtgc agtctg                        46

<210> SEQ ID NO 3
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caattactat ttacaattac aatgcaggtc cagcttgtgc agtctg                        46

<210> SEQ ID NO 4
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caattactat ttacaattac aatgsaggtc cagctggtac agtctg                        46

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caattactat ttacaattac aatgcaratg cagctggtgc agtctg                        46

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caattactat ttacaattac aatgcagrtc accttgaagg agtctg                        46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caattactat ttacaattac aatggargtg cagctggtgg agtctg                46

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caattactat ttacaattac aatgcaggtg cagctggtgg agtctg                46

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
caattactat ttacaattac aatggaggtg cagctgttgg agtctg                46

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
caattactat ttacaattac aatgcagstg cagctgcagg ag                    42

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caattactat ttacaattac aatgcaggtg cagctacagc agtgg                 45

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caattactat ttacaattac aatggargtg cagctggtgc agtctg                46

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caattactat ttacaattac aatgcaggta cagctgcagc agtcag        46

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
caattactat ttacaattac aatgcaggtg cagctggtgc aatctg        46

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taatacgact cactataggg acaattacta tttacaatta ca            42

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gccgtgtatt actgtgc                                        17

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggagacgagg gggaaaaggg ttgaggagac ggtgaccag                39

<210> SEQ ID NO 18
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttttttttt tttttttttt aaatagcgga tgctaaggac gacttgtcgt cgtcgtcctt    60
gtagtcggag acgaggggga aagggt                                        87

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatccctcga                                                              10

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgcccggact c                                                            11

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttcccgatcc ga                                                           12

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
acgtgtctac c                                                            11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aacccaatcc c                                                            11

<210> SEQ ID NO 24
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gacaccgggc cc                                                           12

```
<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctactcctac c                                                              11

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cctccttcga cc                                                             12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccggctttcc aa                                                             12

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cggcttcctg at                                                             12
```